US012770738B2

(12) United States Patent
Tsai

(10) Patent No.: US 12,770,738 B2
(45) Date of Patent: Oct. 20, 2026

(54) ARTIFICIAL INTELLIGENCE-ENABLED ECG ALGORITHM SYSTEM AND METHOD THEREOF

(71) Applicant: National Taiwan University, Taipei City (TW)

(72) Inventor: Chia-Ti Tsai, Taipei City (TW)

(73) Assignee: National Taiwan University, Taipei City (TW)

( * ) Notice: Subject to any disclaimer, the term of this patent is extended or adjusted under 35 U.S.C. 154(b) by 152 days.

(21) Appl. No.: 18/490,918

(22) Filed: Oct. 20, 2023

(65) Prior Publication Data

US 2025/0037859 A1 Jan. 30, 2025

(30) Foreign Application Priority Data

Jul. 26, 2023 (TW) ................................ 112127990

(51) Int. Cl.

| | |
|---|---|
| ***G16H 50/20*** | (2018.01) |
| ***G06N 3/0464*** | (2023.01) |
| ***G06N 3/09*** | (2023.01) |

(52) U.S. Cl.

CPC ........... *G16H 50/20* (2018.01); *G06N 3/0464* (2023.01); *G06N 3/09* (2023.01)

(58) Field of Classification Search

CPC ........ G16H 50/20; G06N 3/09; G06N 3/0464; G06N 3/045; G06N 3/08

See application file for complete search history.

(56) References Cited

U.S. PATENT DOCUMENTS

2022/0370017 A1* 11/2022 DeMazumder ........ A61B 5/318
2023/0245782 A1* 8/2023 Zimmerman ......... G06F 18/214 600/301
2023/0335289 A1* 10/2023 Kuck ..................... G16H 50/20

FOREIGN PATENT DOCUMENTS

WO WO-2021068142 A1 * 4/2021 ......... G06K 9/00442

OTHER PUBLICATIONS

Ullah et al., An Automatic Premature Ventricular Contraction Recognition System Based on Imbalanced Dataset and Pre-Trained Residual Network Using Transfer Learning on ECG Signal, 2022, Diagnostics, 13, 87, pp. 1-20 (Year: 2022).*
TW Shen, TF Laio, Image Processing on ECG Chart for ECG Signal Recovery, 2009, Computers in Cardiology, 36, pp. 725-728. (Year: 2009).*

(Continued)

*Primary Examiner* — Kambiz Abdi
*Assistant Examiner* — Kyra R Lagoy

(57) ABSTRACT

An artificial intelligence-enabled ECG algorithm system and method thereof are applied in the environment of the identification of patients with ventricular premature contractions (VPC) during sinus rhythm. The present invention of the artificial intelligence-enabled ECG algorithm system and method thereof can provide, a standard 10-second, 12-lead ECGs algorithm based on artificial intelligence for the identification of patients with ventricular premature contractions (VPC) during normal sinus rhythm; and, the ECG algorithm using artificial intelligence can detect some minimal changes in the patient's sinus rhythm ECG without VPC episodes, and can also identify patients having ventricular premature contraction for early treatment to reduce the patent's risk of heart failure or sudden death.

8 Claims, 12 Drawing Sheets

(56) References Cited

OTHER PUBLICATIONS

Taeyoung Yoon & Daesung Kang, Bimodal CNN for cardiovascular disease classification by co-training ECG grayscale images and scalograms., 2023, Scientific Reports, 13:2937, pp. 1-9 (Year: 2023).*

Patil et al., Auto Lead Extraction and Digitization of ECG Paper Records Using CGAN, 2022, arXiv preprint, pp. 1-10. (Year: 2022).*

Sheng Nan Chang et al., "An artificial intelligence enabled ECG algorithm for identifying ventricular premature contraction during sinus rhythm", European Journal of Medical Research, Dec. 14, 2022.

* cited by examiner

| 2D CNN model | Accuracy | ROC AUC | Sensitivity | Specificity |
|---|---|---|---|---|
| InceptionV3 + Dense (512) | 0.895 | 0.941 | 0.907 | 0.883 |

ARTIFICIAL INTELLIGENCE-ENABLED ECG ALGORITHM SYSTEM AND METHOD THEREOF

CROSS-REFERENCE TO RELATED APPLICATION

This application claims the priority of Taiwanese patent application No. 112127990, filed on Jul. 26, 2023, which is incorporated herewith by reference.

BACKGROUND OF THE INVENTION

1. Field of the Invention

The present invention relates generally to an electrocardiogram algorithm system and a method thereof, and more particularly, to an artificial intelligence-enabled ECG algorithm system and method thereof applied in the environment of the identification of patients with ventricular premature contractions (VPC) during sinus rhythm; and the ECG algorithm using artificial intelligence to detect some minimal changes in the patient's sinus rhythm ECG without VPC episodes, and also to identify patients having ventricular premature contraction for early treatment to reduce the patent's risk of heart failure or sudden death.

2. The Prior Arts

Modern people are faced with continuous accumulation of various pressures in work and life, resulting in symptoms of arrhythmia, and VPC (VPC) are the clinically common arrhythmias. VPC can induce ventricular tachycardia/fibrillation or VPC-induced cardiomyopathy in susceptible patients. Existing screening methods require prolonged ECG monitoring and are limited by cost and low yield when VPC frequency is low.

Ventricular premature contractions (VPC) are common arrhythmias in the whole world, and according to previous studies, on the standard 12-lead electrocardiogram (ECG), the prevalence rate of VPC in the general population is about 1% to 4%. In addition, various factors, such as, increasing age, male, atherosclerosis, hypertension, and cardiomyopathy are all associated with an increased incidence of VPC.

Clinically, VPC without any symptoms seem to be benign, yet frequent VPC attacks are related to cardiomyopathy and irreversible pathogenesis, especially in patients with structural heart disease. The incidence and complexity of VPC are also increasing, reaching up to 90% in ischemic cardiomyopathy.

Thus, VPC appears to be a signal of increased risk of sudden death or a clue to underlying cardiomyopathy. Therefore, timely prediction and intervention of VPC episodes may eliminate possible arrhythmic source and reverse progressive cardiomyopathy.

Clinically, traditional 12-lead ECGs have been used to monitor heart structure and physiological conditions for decades, and electrocardiograms are non-invasive, easy to use, fast, cost-effective in facility, and easy to explain.

Due to these features, some ECG monitoring systems are used to analyze the ECG signal. To quickly interpret these massive amounts of data, deep learning has been widely used to read ECG signals, while artificial intelligence (AI) technology is adapted to process countless ECG signals and automatically provide accurate diagnoses without human intervention.

However, intermittent VPC occur in most patients, and occasionally, all ECG-related examinations or monitoring are negative for the definite diagnosis of VPC.

In related research, a paper titled "An artificial intelligence-enabled ECG algorithm for the identification of patients with atrial fibrillation during sinus rhythm: a retrospective analysis of outcome prediction" disclosed that "an artificial intelligence-enabled ECG algorithm (ECG) used a convolutional neural network to detect ECG signatures of atrial fibrillation during normal sinus rhythm using a standard 10-second, 12-lead ECG."

However, the aforementioned paper did not disclose the technical features and contents of: "An artificial intelligence-enabled ECG algorithm was developed using convolutional neural networks to detect ventricular abnormalities during normal sinus rhythm using a standard 10-second, 12-lead ECG features. Both image and time series datasets were parsed for CNN training. The computer architecture was optimized to select the best model for the training process. Single input image model (InceptionV3, accuracy: 0.895, 95% interval [CI] 0.683-0.937) and multi-input time series model (ResNet50V2, accuracy: 0.88, 95% CI 0.646-0.943) are both found to show satisfactory results in predicting VPC, both are better than single-input time series model (ResNet50V2, accurate Rate: 0.84, 95% CI 0.629-0.952)".

Therefore, there are remaining issues to be addressed, including: how can a tool be used to identify VPC patients using ECG during sinus rhythm, an AI-enabled ECG algorithm can be used to identify paroxysmal VPC patients during sinus rhythm; how can an automated deep learning neural network be used to identify high-risk VPC populations, using their ECG during sinus rhythm during the absence of VPC, to facilitate the point of care and hopefully prevent serious cardiovascular events in advance; how to obtain the AI-enabled ECG during sinus rhythm to allow rapid identification of individuals with VPC at the point of care and to automatically predict the potential VPC onset, rather than traditional long-term monitoring; based on the low cost, speed, and wide application, how AI and machine learning-enabled ECG readings can be used to identify VPC patients during normal sinus rhythm (NSR); and, how to disclose technical features and contents not available in patent or non-patent literatures: "Developing an AI-enabled ECG algorithm by using convolutional neural networks to detect ECG subtle features of VPC that are present during normal sinus rhythm using a standard 10-second, 12-lead ECG. Moreover, for example, multiple patients (e.g., 398) were diagnosed with VPC from which multiple ECG records were collected (e.g., 2,515). ECG records (e.g., 1617 ECG records) in normal sinus rhythm without VPC were parsed, and multiple normal ECG records (e.g., 753) from multiple patients (e.g., 387) in normal sinus rhythm were analyzed. In comparison, both image and time-series datasets were parsed for CNN training, while the computer architecture was optimized to select the best model for the training process, and a single-input image model (InceptionV3, accuracy: 0.895, 95% interval [CI] 0.683-0.937) and multi-input time series model (ResNet50V2, accuracy: 0.88, 95% CI 0.646-0.943) can both show satisfactory results in predicting VPC, better than single-input time series model (ResNet50V2, accurate Rate: 0.84, 95% CI 0.629-0.952)."

SUMMARY OF THE INVENTION

A primary objective of the present invention is to provide an artificial intelligence-enabled electrocardiogram (ECG)

algorithm system and method thereof, which is applied to identify VPC patients in the environment during sinus rhythm, the artificial intelligence-enabled ECG algorithm system and method thereof of the present invention can provide, an artificial intelligence-enabled standard 10-second, 12-lead ECG algorithm for identifying VPC patients during normal sinus rhythm; the ECG algorithm using artificial intelligence can detect some minimal changes in the patient's sinus rhythm ECG, and also identify patients with VPC, so that the early treatment can reduce the risk of heart failure or sudden death of the patients.

Another objective of the present invention is to provide an artificial intelligence-enabled ECG algorithm system and method thereof, applicable to identifying VPC patients in the environment during sinus rhythm based on the 10-second, 12-lead ECG, which is low-cost, fast, and widely used, and can use AI and machine learning-enabled ECG readings to identify VPC patients during the period normal sinus rhythm (NSR).

Another objective of the present invention is to provide an artificial intelligence-enabled ECG algorithm system and method thereof, applicable to identifying VPC patients in the environment during sinus rhythm, to address the following issues: using an AI-enabled ECG algorithm to identify paroxysmal VPC patients during sinus rhythm; using an automated deep learning neural network be used to identify high-risk VPC populations, using their ECG during sinus rhythm during the absence of VPC, to facilitate the point of care and hopefully prevent serious cardiovascular events in advance; obtaining the AI-enabled ECG during sinus rhythm to allow rapid identification of individuals with VPC at the point of care and to automatically predict the potential VPC onset, rather than traditional long-term monitoring.

Another objective of the present invention is to provide an artificial intelligence-enabled ECG algorithm system and method thereof, applicable to identifying VPC patients in the environment during sinus rhythm, and disclosing technical features and contents not available in patent or non-patent literatures: "Developing an AI-enabled ECG algorithm by using convolutional neural networks to detect ECG subtle features of VPC that are present during normal sinus rhythm using a standard 10-second, 12-lead ECG. Moreover, for example, multiple patients (e.g., 398) were diagnosed with VPC from which multiple ECG records were collected (e.g., 2,515). ECG records (e.g., 1617 ECG records) in normal sinus rhythm without VPC were parsed, and multiple normal ECG records (e.g., 753) from multiple patients (e.g., 387) in normal sinus rhythm were analyzed. In comparison, both image and time-series datasets were parsed for CNN training, while the computer architecture was optimized to select the best model for the training process, and a single-input image model (InceptionV3, accuracy: 0.895, 95% interval [CI] 0.683-0.937) and multi-input time series model (ResNet50V2, accuracy: 0.88, 95% CI 0.646-0.943) can both show satisfactory results in predicting VPC, better than single-input time series model (ResNet50V2, accurate Rate: 0.84, 95% CI 0.629-0.952)."

According to the aforementioned objectives, the present invention provides an artificial intelligence-enabled ECG algorithm system including an information processing module, a convolutional neural network (CNN) module, and a database.

The information processing module: the information processing module cooperates with the CNN module and the database, classifies data stored and temporarily stored in the database, divides the data into a training set, a validation set, and a test set, and processes the data of the training set, validation set, and test set, so that these processed data are sent to the CNN module to allow the CNN module to use the artificial intelligence-enabled electrocardiogram algorithm system and method of the present invention to generate an evaluation model for identifying VPC patients during NSR period for the CNN module.

The CNN module: the information processing module transmits the processed data to the CNN module, so that the CNN module can use the artificial intelligence-enabled electrocardiogram algorithm system and method of the present invention to generate an evaluation model for identifying VPC patients during NSR period for the CNN module; the CNN module uses the evaluation model for identifying VPC patients during NSR, in combination with the information processing module and the patient data stored in the database, to detect some minimal change in the electrocardiogram of sinus rhythm when the patient is without VPC episodes so that early treatment can provided to reduce the risk of heart failure or sudden death in patients.

The database: the database can store and/or temporarily store datasets, and the datasets are divided into training sets, validation sets, and test sets, depending on actual applications; and also store/temporarily store the datasets of the patients, the artificial intelligent-enabled ECG algorithm of the present invention, and the evaluation model for identifying VPC patients during NSR.

When using the artificial intelligence-enabled ECG algorithm system of the present invention to carry out the process of the artificial intelligence-enabled ECG algorithm method: first, perform data collection and analysis steps; when the information processing module performs the data collection and analysis step, the information processing module cooperates with the database and/or the CNN module to collect data, for example, the data are collected from January 2021 to October 2021 on the patients diagnosed with VPC. Initially, 398 patients were diagnosed with VPC, and from which 2515 ECG records were collected and examined. 1617 ECG records in normal sinus rhythm without VPC are analyzed (i.e., the ECG records from patients not diagnosed with VPC), and these 1617 ECG records were double-checked by two cardiologists, and labeled as sinus rhythm from patients with VPC. For the control group, 2090 ECG records from 1053 patients were collected and screened; and finally, 753 normal ECG records from 387 patients were extracted and labeled as normal sinus rhythm (NSR). After finishing the data collection and analysis step, all the data will be stored/temporarily stored in the database.

Then, the dataset preparation step is performed, wherein the information processing module cooperates with the database and/or the CNN module to classify and divide the datasets stored/temporarily stored in the database into a training set, a validation set, and a test set. First, 50 ECG records are randomly selected as the validation set, another 100 ECG records are selected as the test set, and the remaining data are assigned to the training set. It is important that data from the same patient cannot be in more than one dataset, otherwise the credibility of the final results will be affected.

Furthermore, data types and preprocessing steps are performed, wherein the information processing module cooperates with the database and/or the CNN module to adopt a standard 12-lead electrocardiogram format, including lead I, II, III, V1~6, aVR, aVL, aVF, and long lead II (MAC2000 resting ECG system, GE Healthcare), all recorded at a frequency of 500 Hz for a duration of 2.5 seconds for the collected electrocardiogram records.

During the electrocardiogram image processing procedure before the electrocardiogram image data output, the red grid background of the electrocardiogram image is removed and processed, so that the entire image is accurately focused on the electrocardiogram signal; including, inputting the standard 12-lead electrocardiogram image; removing the red background of the 12-lead ECG image; cropping the image to focus on the ECG signal.

Afterwards, the information processing module adjusts the electrocardiogram image to 512×256×3 pixels, and the two-dimensional electrocardiogram image is converted into one-dimensional time series data; an input data size of 1250×12 pixels is inputted to the CNN of the CNN module to perform image recognition.

Converting 2D ECG image to 1D time-series digital data with the ECG data input format is as follows:

a. Remove the red grid background of the 12-lead ECG, and convert the ECG image to a grayscale image;
b. Inverse the pixel intensity of the gray scale image, and scale the pixel intensity to a gray level between 0 to 255. Cut the image vertically into four sub-images according to the "start" and "end" positions of each lead. The four sub-images contain 4 ECG tracings;
c. Scan the sub-image pixel-by-pixel and record the positions of the pixels where the pixel intensity is equal to 255, which are the brightest pixels representing ECG tracings. For each detected brightest pixel, the X-coordinate is assigned as the corresponding time point and the Y-coordinate as the waveform amplitude of an ECG data point;
d. The pixel coordinates of the ECG data points are then sequentially grouped to reconstruct a continuous ECG signal, and the 2D ECG image is thus digitized into 1D time-series data;
e. After pixel-by-pixel scanning again, the X-coordinate of the 1D time-series data is formatted to 250 pixels (250 time points for each ECG tracing). The interpolation operation is used to perform up-sampling on the time series data to obtain 1250 time points, corresponding to sampling at a standard 12-lead ECG sampling rate (500 Hz, 2.5 seconds);
f. IIR low-pass filter is used for filtering noise (cutoff frequency=15 Hz, order=3); and
g. Normalize the magnitude of each ECG lead tracing to a uniform scale.

Then, the model process step is performed, wherein the information processing module cooperates with the database and/or the CNN module, and the CNN module utilizes algorithm of the present invention to establish an evaluation model for identifying VPC patients during NSR required by the CNN module, which will be established based on the dimensional features of the data format. For two-dimensional image data, five network computer architectures are used, including VGG16, ResNet0V2, InceptionV3, InceptionResNetV2, and Xception, to utilize the ImageNet part of the CNN for optimal image recognition.

The structure of CNN:

a. Two-dimensional image data is processed through five network computer architectures including VGG16, ResNet50V2, Inception V3, InceptionResNetV2, and Xception to obtain the optimal image recognition in the ImageNet part of CNN, and then flatten into GlobalAveragePooling (GAP); CNN, after extracting the features of the image data, flattens the signal by busing GlobalAveragePooling (GAP), and connects to another dense layer; Dropout is added to avoid overfitting later (dropout rate=0.5); and finally, another dense layer of size 2 is added, which presents two types of results as an output layer (VPC and NSR);
b. A dense layer is connected with a single input from 2D image data; dropout is added to avoid overfitting (dropout rate=0.5), and another dense layer of size 2 is added to obtain an output layer (VPC: Ventricular premature contractions; NOR: normal rhythm); for time series data, performing model processing by using single-input and multi-input computer architectures; initially, the convolution kernel (kernel) is changed to a one-dimensional kernel, and CNN tries different kernel sizes; stride is set to 3, and the moving window of the convolution kernel spans three grids at a time; each convolution block comprises a one-dimensional CNN activated by BatchNormalization and ReLU; the setting of Maxpooling is that the pooling size is equal to 5, and the stride is equal to 3; the feature signal is extracted by the CNN layer, and then flattened by GAP; the output features of the single-input model are directly connected to dropout (dropout rate=0.5) to avoid overfitting; on the other hand, the multi-input model will merge the features of the 12 channels together and connect to a dense layer (dense size=2) to obtain the output result;
c. The signal of time series data is extracted by CNN layer and then flattened by GAP. The output features of the single-input model are directly connected to dropout (dropout rate=0.5), and the multi-input model of the features of 12 channels is merged to obtain the output result (dense size=2), (GAP is the global average pool).

Then, a training procedure step is performed, wherein Google Colaboratory (Colab) with a high random access memory graphics processing unit environment is used as a training platform; the Colab is supported by Python 3.8 and Tensorflow for CNN training process.

The keras application programming interface (API), which is a deep learning API written in Python, is also used to build CNN models and ImageNet races for migration and learning.

Finally, a statistical analysis step is performed, wherein optimal cut points and measures for diagnosing the performance include accuracy, sensitivity, specificity, positive predictive value, negative predictive value, and area under the curve (AUC) of receiver operating feature (ROC) curve. All reports have two-sided 95% confidence intervals. Data were statistically analyzed by IBM SPSS (version 25 for Windows, Armonk, New York).

In order to make those familiar with the art understand the purpose, features and effects of the present invention, the present invention is described in detail as follows by following specific examples, and in conjunction with the accompanying drawings:

DETAILED DESCRIPTION OF THE PREFERRED EMBODIMENT

The accompanying drawings are included to provide a further understanding of the invention, and are incorporated in and constitute a part of this specification. The drawings illustrate embodiments of the invention and, together with the description, serve to explain the principles of the invention.

Figure 1:
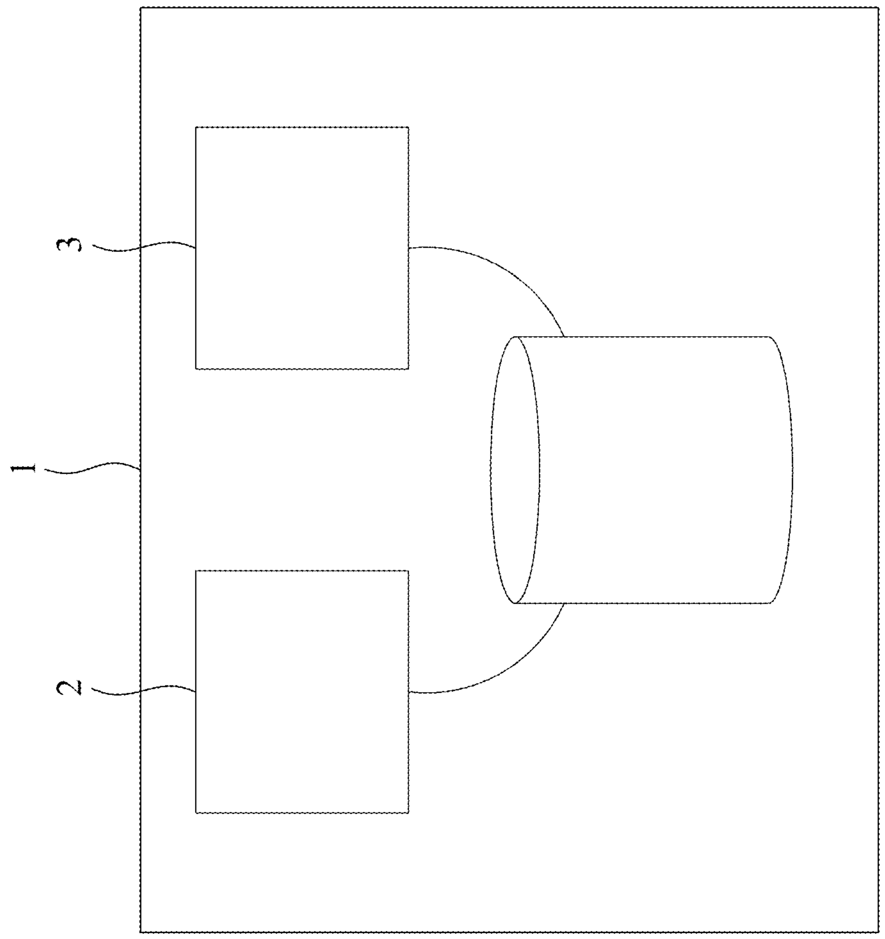
FIG. 1 is a schematic view of the system, which is used to illustrate the system architecture and operation of the artificial intelligence-enabled electrocardiogram algorithm system of the present invention.

FIG. 1 is a schematic view of a system for illustrating the system architecture and operation of the artificial intelligence-enabled electrocardiogram algorithm system of the present invention. As shown in FIG. 1, the artificial intelligence-enabled ECG algorithm system 1 includes an information processing module 2, a convolutional neural network (CNN) module 3, and a database 4.

The information processing module 2: the information processing module 2 cooperates with the CNN module 3 and the database 4, classifies data stored and temporarily stored in the database, divides the data into a training set, a validation set, and a test set, and processes the data of the training set, validation set, and test set, so that these processed data are sent to the CNN module 3 to allow the CNN module 3 to use the artificial intelligence-enabled electrocardiogram algorithm system and method of the present invention to generate an evaluation model for identifying VPC patients during NSR period for the CNN module.

The CNN module 3: the information processing module 2 transmits the processed data to the CNN module 3, so that the CNN module 3 can use the artificial intelligence-enabled electrocardiogram algorithm system and method of the present invention to generate an evaluation model for identifying VPC patients during NSR period for the CNN module 3; the CNN module 3 uses the evaluation model for identifying VPC patients during NSR, in combination with the information processing module 2 and the patient data stored in the database 4, to detect some minimal change in the electrocardiogram of sinus rhythm when the patient is without VPC episodes so that early treatment can provided to reduce the risk of heart failure or sudden death in patients.

The database 4: the database 4 can store and/or temporarily store datasets, and the datasets are divided into training sets, validation sets, and test sets, depending on actual applications, and also store/temporarily store the datasets of the patients, the artificial intelligent-enabled ECG algorithm of the present invention, and the evaluation model for identifying VPC patients during NSR.

Depending on the implementation, the information processing module 2 and/or the CNN module 3 comprise at least one of electronic hardware, firmware, and software, and cooperates with the processor (not shown) of the system/device where the artificial intelligence-enabled electrocardiogram algorithm system 1 is located; and the database 4 is located in a storage module (not shown) of the system/device where the artificial intelligence-enabled electrocardiogram algorithm system 1 is located.

Herein, during actual implementation, the information processing module 2 cooperates with the database 4 and/or the CNN module 3 to collect data. For example, the data are collected from January 2021 to October 2021 on the patients diagnosed with VPC from the National Taiwan University Hospital. Initially, 398 patients were diagnosed with VPC, and from which 2515 ECG records were collected and examined. 1617 ECG records in normal sinus rhythm without VPC are analyzed (i.e., the ECG records from patients not diagnosed with VPC), and these 1617 ECG records were double-checked by two cardiologists, and labeled as sinus rhythm from patients with VPC. For the control group, 2090 ECG records from 1053 patients were collected and screened; and finally, 753 normal ECG records from 387 patients were extracted and labeled as normal sinus rhythm (NSR). After finishing the data collection and analysis step, all the data will be stored/temporarily stored in the database 4.

The information processing module 2 cooperates with the database 4 and/or the CNN module 3 to classify and divide the data stored/temporarily stored in the database 4 into a training set, a validation set, and a test set. First, 50 ECG records are randomly selected as the validation set, another 100 ECG records are selected as the test set, and the remaining ECG records are assigned to the training set. It is important that data from the same patient cannot be in more than one dataset, otherwise the credibility of the final results will be affected.

The information processing module 2 cooperates with the database 4 and/or the CNN module 3, and adopts the standard 12-lead ECG format for the collected ECG records, including leads I, II, III, V1-6. aVR, aVL, aVF and long lead II (MAC2000 resting ECG system, GE Healthcare), all recorded at a frequency of 500 Hz and for a duration of 2.5 seconds.

Herein, during the electrocardiogram image processing procedure before the electrocardiogram image data output, the red grid background of the electrocardiogram image is removed and processed, so that the entire image is accurately focused on the electrocardiogram signal; including, inputting the standard 12-lead electrocardiogram image; removing the red background of the 12-lead ECG image; cropping the image to focus on the ECG signal.

Afterwards, the information processing module adjusts the electrocardiogram image to 512×256×3 pixels, and the two-dimensional electrocardiogram image is converted into one-dimensional time series data; an input data size of 1250×12 pixels is inputted to the CNN of the CNN module 3 to perform image recognition.

Converting 2D ECG image to 1D time-series digital data with the ECG data input format is as follows:

a. Remove the red grid background of the 12-lead ECG, and convert the ECG image to a grayscale image;

b. Inverse the pixel intensity of the gray scale image, and scale the pixel intensity to a gray level between 0 to 255. Cut the image vertically into four sub-images according to the "start" and "end" positions of each lead. The four sub-images contain 4 ECG tracings;

c. Scan the sub-image pixel-by-pixel and record the positions of the pixels where the pixel intensity is equal to 255, which are the brightest pixels representing ECG tracings. For each detected brightest pixel, the X-coordinate is assigned as the corresponding time point and the Y-coordinate as the waveform amplitude of an ECG data point;

d. The pixel coordinates of the ECG data points are then sequentially grouped to reconstruct a continuous ECG signal, and the 2D ECG image is thus digitized into 1D time-series data;

e. After pixel-by-pixel scanning again, the X-coordinate of the 1D time-series data is formatted to 250 pixels (250 time points for each ECG lead tracing). The interpolation operation is used to perform up-sampling on the time series data to obtain 1250 time points, corresponding to sampling at a standard 12-lead ECG sampling rate (500 Hz, 2.5 seconds);

f. IIR low-pass filter is used for filtering noise (cutoff frequency=15 Hz, order=3); and g. Normalize the magnitude of each ECG lead tracing to a uniform scale.

The information processing module 2 cooperates with the database 4 and/or the CNN module 3, and the CNN module 3 utilizes algorithm of the present invention to establish an evaluation model for identifying VPC patients during NSR required by the CNN module 3, which will be established based on the dimensional features of the data format. Herein, for two-dimensional image data, five network computer architectures are used, including VGG16, ResNet0V2, InceptionV3, InceptionResNetV2, and Xception, to utilize the ImageNet part of the CNN for optimal image recognition.

The structure of CNN:

a. Two-dimensional image data is processed through five network computer architectures including VGG16, ResNet50V2, Inception V3, InceptionResNetV2, and Xception to obtain the optimal image recognition in the ImageNet part of CNN, and then flatten into GlobalAveragePooling (GAP); CNN, after extracting the features of the image data, flattens the signal by busing GlobalAveragePooling (GAP), and connects to another dense layer; Dropout is added to avoid overfitting later (dropout rate=0.5); and finally, another dense layer of size 2 is added, which presents two types of results as an output layer (VPC and NSR);

b. A dense layer is connected with a single input from 2D image data; dropout is added to avoid overfitting (dropout rate=0.5), and another dense layer of size 2 is added to obtain an output layer (VPC: Ventricular premature contractions; NOR: normal rhythm); for time series data, performing model processing by using single-input and multi-input computer architectures; initially, the convolution kernel (kernel) is changed to a one-dimensional kernel, and CNN tries different kernel sizes; stride is set to 3, and the moving window of the convolution kernel spans three grids at a time; each convolution block comprises a one-dimensional CNN activated by BatchNormalization and ReLU; the setting of Maxpooling is that the pooling size is equal to 5, and the stride is equal to 3; the feature signal is extracted by the CNN layer, and then flattened by GAP; the output features of the single-input model are directly connected to dropout (dropout rate=0.5) to avoid overfitting; on the other hand, the multi-input model will merge the features of the 12 channels together and connect to a dense layer (dense size=2) to obtain the output result;

c. The signal of time series data is extracted by CNN layer and then flattened by GAP. The output features of the single-input model are directly connected to dropout (dropout rate=0.5), and the multi-input model of the features of 12 channels is merged to obtain the output result (dense size=2), (GAP is the global average pool).

During a training procedure, Google Colaboratory (Colab) with a high random access memory graphics processing unit environment is used as a training platform; the Colab is supported by Python 3.8 and Tensorflow for CNN training process.

The keras application programming interface (API), which is a deep learning API written in Python, is also used to build CNN models and ImageNet races for migration and learning.

During statistical analysis, the optimal cut points and measures for diagnosing the performance include accuracy, sensitivity, specificity, positive predictive value, negative predictive value, and area under the curve (AUC) of receiver operating feature (ROC) curve. All reports have two-sided 95% confidence intervals. Data were statistically analyzed by IBM SPSS (version 25 for Windows, Armonk, New York).

The artificial intelligence-enabled ECG algorithm system and method thereof of the present invention is applied to identify VPC patients in the environment during sinus rhythm, the artificial intelligence-enabled ECG algorithm system and method thereof of the present invention can provide, an artificial intelligence-enabled standard 10-second, 12-lead ECG algorithm for identifying VPC patients during normal sinus rhythm; the ECG algorithm using artificial intelligence can detect some minimal changes in the patient's sinus rhythm ECG, and also identify patients with VPC, so that the early treatment can reduce the risk of heart failure or sudden death of the patients.

Also, the artificial intelligence-enabled ECG algorithm system and method thereof of the present invention is applicable to identifying VPC patients in the environment during sinus rhythm based on the 10-second, 12-lead ECG, which is low-cost, fast, and widely used, and can use AI and machine learning-enabled ECG readings to identify VPC patients during the period normal sinus rhythm (NSR).

Furthermore, the artificial intelligence-enabled ECG algorithm system and method thereof of the present invention is applicable to identifying VPC patients in the environment during sinus rhythm, to address the following issues: using an AI-enabled ECG algorithm to identify paroxysmal VPC patients during sinus rhythm; using an automated deep learning neural network be used to identify high-risk VPC populations, using their ECG during sinus rhythm during the absence of VPC, to facilitate the point of care and hopefully prevent serious cardiovascular events in advance; obtaining the AI-enabled ECG during sinus rhythm to allow rapid identification of individuals with VPC at the point of care and to automatically predict the potential VPC onset, rather than traditional long-term monitoring.

Moreover, the artificial intelligence-enabled ECG algorithm system and method thereof of the present invention is applicable to identifying VPC patients in the environment during sinus rhythm, and disclosing technical features and contents not available in patent or non-patent literatures: "Developing an AI-enabled ECG algorithm by using convolutional neural networks to detect ECG subtle features of VPC that are present during normal sinus rhythm using a standard 10-second, 12-lead ECG. Moreover, for example, multiple patients (e.g., 398) were diagnosed with VPC from which multiple ECG records were collected (e.g., 2,515). ECG records (e.g., 1617 ECG records) in normal sinus rhythm without VPC were parsed, and multiple normal ECG records (e.g., 753) from multiple patients (e.g., 387) in normal sinus rhythm were analyzed. In comparison, both image and time-series datasets were parsed for CNN training, while the computer architecture was optimized to select the best model for the training process, and a single-input image model (InceptionV3, accuracy: 0.895, 95% interval [CI] 0.683-0.937) and multi-input time series model (ResNet50V2, accuracy: 0.88, 95% CI 0.646-0.943) can both show satisfactory results in predicting VPC, better than single-input time series model (ResNet50V2, accurate Rate: 0.84, 95% CI 0.629-0.952)."

Figure 2:
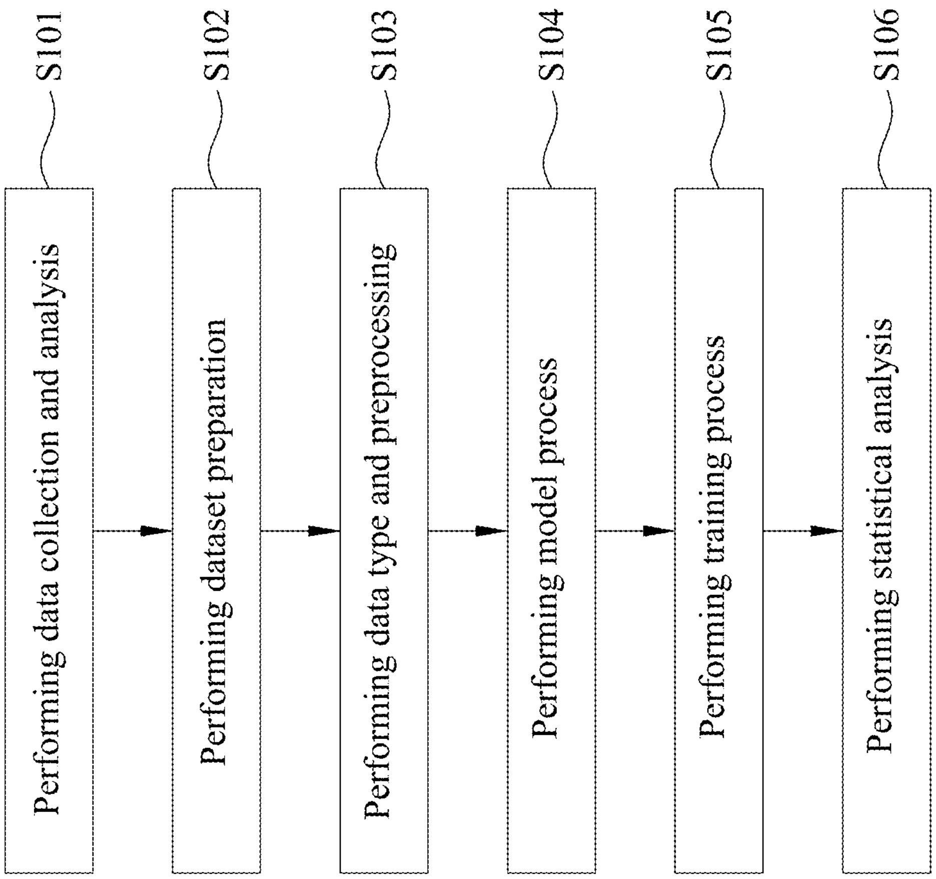
FIG. 2 is a flow chart illustrating a process step of using the artificial intelligence-enabled electrocardiogram algorithm system of the present invention as in FIG. 1 to perform an artificial intelligence-enabled ECG algorithm method.

FIG. 2 is a flow chart illustrating a process step of using the artificial intelligence-enabled ECG algorithm system of the present invention as in FIG. 1 to execute the artificial intelligence-enabled ECG algorithm method. As shown in FIG. 2, first, step 101 is to perform data collection and analysis, wherein when the information processing module 2 performs the data collection and analysis, the information processing module 2 cooperates with the database 4 and/or the CNN module 3 to collect data; and then proceed to step 102.

Herein, in step 101, when the information processing module 2 performs data collection and analysis, the information processing module 2 cooperates with the database 4 and/or the CNN module 3 to collect data. For example, the data are collected from January 2021 to October 2021 on the patients diagnosed with VPC from the National Taiwan University Hospital. Initially, 398 patients were diagnosed with VPC, and from which 2515 ECG records were collected and examined. 1617 ECG records in normal sinus rhythm without VPC are analyzed (i.e., the ECG records from patients not diagnosed with VPC), and these 1617 ECG records were double-checked by two cardiologists, and labeled as sinus rhythm from patients with VPC. For the control group, 2090 ECG records from 1053 patients were collected and screened; and finally, 753 normal ECG records from 387 patients were extracted and labeled as normal sinus rhythm (NSR). After finishing the data collection and analysis step, all the data will be stored/temporarily stored in the database 4.

Step 102 is to prepare the data, wherein the information processing module 2 cooperates with the database 4 and/or the CNN module 3 to classify and divide the data stored/temporarily stored in the database 4 into a training set, a validation set, and a test set; and then proceed to step 103.

Herein, in step 102, 50 ECG records are randomly selected as a validation set, and 100 ECG records are selected as a test set, and the remaining data are assigned to the training set. It is important that data from the same patient cannot be in more than one dataset, otherwise the credibility of the final results will be affected.

Step 103 is to perform data type and preprocessing, wherein the information processing module 2 cooperates with the database 4 and/or the CNN module 3, and adopts the standard 12-lead ECG format for the collected ECG records, including leads I, II, III, V1-6, aVR, aVL, aVF and long lead II (MAC2000 resting ECG system, GE Healthcare), and all recordings are measured at a frequency of 500 Hz with a duration of 2.5 seconds; and then proceed to step 104.

Herein, in step 103, during the electrocardiogram image processing procedure before the electrocardiogram image data output, the red grid background of the electrocardiogram image is removed and processed, so that the entire image is accurately focused on the electrocardiogram signal; including, inputting the standard 12-lead electrocardiogram image; removing the red background of the 12-lead ECG image; cropping the image to focus on the ECG signal.

Afterwards, the information processing module adjusts the electrocardiogram image to 512×256×3 pixels, and the two-dimensional electrocardiogram image is converted into one-dimensional time series data; an input data size of 1250×12 pixels is inputted to the CNN of the CNN module 3 to perform image recognition.

Converting 2D ECG image to 1D time-series digital data with the ECG data input format is as follows:

a. Remove the red grid background of the 12-lead ECG, and convert the ECG image to a grayscale image;
b. Inverse the pixel intensity of the gray scale image, and scale the pixel intensity to a gray level between 0 to 255. Cut the image vertically into four sub-images according to the "start" and "end" positions of each lead. The four sub-images contain 4 ECG tracings;
c. Scan the sub-image pixel-by-pixel and record the positions of the pixels where the pixel intensity is equal to 255, which are the brightest pixels representing ECG tracings. For each detected brightest pixel, the X-coordinate is assigned as the corresponding time point and the Y-coordinate as the waveform amplitude of an ECG data point;
d. The pixel coordinates of the ECG data points are then sequentially grouped to reconstruct a continuous ECG signal, and the 2D ECG image is thus digitized into 1D time-series data;
e. After pixel-by-pixel scanning again, the X-coordinate of the 1D time-series data is formatted to 250 pixels (250 time points for each ECG lead tracing). The interpolation operation is used to perform up-sampling on the time series data to obtain 1250 time points, corresponding to sampling at a standard 12-lead ECG sampling rate (500 Hz, 2.5 seconds);
f. IIR low-pass filter is used for filtering noise (cutoff frequency=15 Hz, order=3); and
g. Normalize the magnitude of each ECG lead tracing to a uniform scale.

Step 104 is to perform the model process, wherein the information processing module 2 cooperates with the database 4 and/or the CNN module 3, and the CNN module 3 utilizes algorithm of the present invention to establish an evaluation model for identifying VPC patients during NSR required by the CNN module 3, which will be established based on the dimensional features of the data format. Herein, for two-dimensional image data, five network computer architectures are used, including VGG16, ResNet0V2, InceptionV3, InceptionResNetV2, and Xception, to utilize the ImageNet part of the CNN for optimal image recognition; and then proceed to step 105.

Herein, the structure of CNN:

a. Two-dimensional image data is processed through five network computer architectures including VGG16, ResNet50V2, Inception V3, InceptionResNetV2, and Xception to obtain the optimal image recognition in the ImageNet part of CNN, and then flatten into GlobalAveragePooling (GAP); CNN, after extracting the features of the image data, flattens the signal by busing GlobalAveragePooling (GAP), and connects to another dense layer; Dropout is added to avoid overfitting later (dropout rate=0.5); and finally, another dense layer of size 2 is added, which presents two types of results as an output layer (VPC and NSR);

b. A dense layer is connected with a single input from 2D image data; dropout is added to avoid overfitting (dropout rate=0.5), and another dense layer of size 2 is added to obtain an output layer (VPC: Ventricular premature contractions; NOR: normal rhythm); for time series data, performing model processing by using single-input and multi-input computer architectures; initially, the convolution kernel (kernel) is changed to a one-dimensional kernel, and CNN tries different kernel sizes; stride is set to 3, and the moving window of the convolution kernel spans three grids at a time; each convolution block comprises a one-dimensional CNN activated by BatchNormalization and ReLU; the setting of Maxpooling is that the pooling size is equal to 5, and the stride is equal to 3; the feature signal is extracted by the CNN layer, and then flattened by GAP; the output features of the single-input model are directly connected to dropout (dropout rate=0.5) to avoid overfitting; on the other hand, the multi-input model will merge the features of the 12 channels together and connect to a dense layer (dense size=2) to obtain the output result;

c. The signal of time series data is extracted by CNN layer and then flattened by GAP. The output features of the single-input model are directly connected to dropout (dropout rate=0.5), and the multi-input model of the features of 12 channels is merged to obtain the output result (dense size=2), (GAP is the global average pool).

Step 105 is to perform a training procedure, wherein Google Colaboratory (Colab) with a high random access memory graphics processing unit environment is used as a training platform; the Colab is supported by Python 3.8 and Tensorflow for CNN training process. The keras application programming interface (API), which is a deep learning API written in Python, is also used to build CNN models and ImageNet races for migration and learning; and then proceed to step 106.

Step 106 is to perform statistical analysis, wherein the optimal cut points and measures for diagnosing the performance include accuracy, sensitivity, specificity, positive predictive value, negative predictive value, and area under the curve (AUC) of receiver operating feature (ROC) curve. All reports have two-sided 95% confidence intervals. Data were statistically analyzed by IBM SPSS (version 25 for Windows, Armonk, New York).

Figure 3:
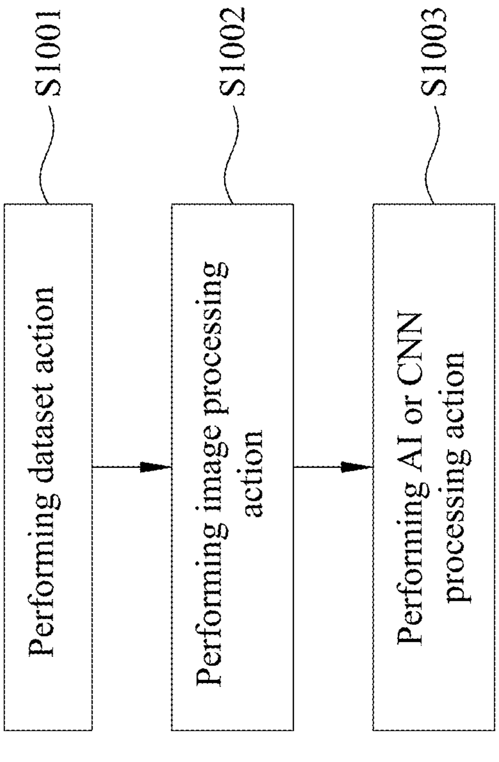
FIG. 3 is a flow chart illustrating another process step of using the artificial intelligence-enabled electrocardiogram algorithm system of the present invention as in FIG. 1 to perform an artificial intelligence-enabled electrocardiogram algorithm method.

FIG. 3 is a flow chart illustrating another process step of using the artificial intelligence-enabled ECG algorithm system of the present invention as in FIG. 1 to execute the Artificial intelligence-enabled ECG algorithm method. As shown in FIG. 3, first, step 1001 is to form the datasets on the data in the database 4; wherein the information processing module 2 cooperates with the database 4 and/or the CNN module 3 to classify and divide the data stored/temporarily stored in the database 4 into a training set, a validation set, and a test set; and then proceed to step 1002.

Herein, the data of the dataset can be one-dimensional (1D) ECG raw data and/or two-dimensional ECG images from the ECG machine, wherein, in terms of the dimensions of the 12-lead ECG data:

When applying CNN analysis in a 12-lead ECG, the 1D approach treats the ECG data as a time-series format. CNNs, on the other hand, use kernels during 2D data processing to extract all the features of a 12-lead ECG. CNN kernels can be activated by specific functions and then identified by neural network analysis.

Therefore, 2D analysis treats the data as an image, more akin to how a cardiologist interprets a 12-lead ECG. However, the 2D data volume is huge and much more complex than the 1D data format.

Step 1002 is to perform the image processing, wherein the information processing module 2 cooperates with the database 4 and/or the CNN module 3 to remove the background (such as red grid) from the ECG data of the collected dataset, which can be an ECG machine 1D raw data and/or 2D ECG image, and the image is resized to make the entire image accurately focused on the ECG signal; and then proceed to step 1003.

Step 1003 is to perform AI or CNN processing, wherein the information processing module 2 cooperates with the database 4 and/or the CNN module 3, and the CNN module 3 utilizes the artificial intelligence-enabled ECG algorithm system and the AI ECG algorithm of the method of the present invention to establish the evaluation model required by the CNN module 3 for identifying VPC patients during NSR. Herein, for example, the established evaluation model for identifying VPC patients during NSR is the CNN model based on the preprocessed ECG 2D data, the dimensional features of the data format, and for ECG 2D image data five network computer architectures including VGG16, ResNet0V2, Inception V3, InceptionResNetV2, and Xception are used to obtain the optimal image recognition using the ImageNet part of CNN.

In step 1003, the common AI tools cannot analyze the 12-lead ECG stored in image format. To overcome the difficulties in analyzing these large and complex 2D data, various combinations of available networks and different computer architectures are used to obtain the most accuracy for VPC predictions of CNN models.

One of the important features of the present invention is the CNN-enabled 2D data prediction VPC model, which has never been successfully performed by prior arts. After optimizing the input model architecture, the two-dimensional CNN model of the present invention can identify abnormal ECG and classify high-risk groups without VPC episodes.

Previous studies show that AI-driven algorithms have been applied to automatic diagnosis of various diseases, such as myocardial infarction requiring urgent blood line reconstitution, systolic heart failure, subtle changes in potassium and atrial fibrillation in high-risk groups.

However, most of these studies are based on single-lead ECG or one-dimensional (i.e., time series) datasets. According to the results of the present invention, CNN models derived from 12-lead ECG and 2D data formats are able to reliably and automatically predict VPC onset with even better accuracy than 1D or time series results (0.895 vs. 0.880). The present invention demonstrates the feasibility of implementing a CNN model to identify VPC patients using 1D or 2D ECG data.

Figure 4:
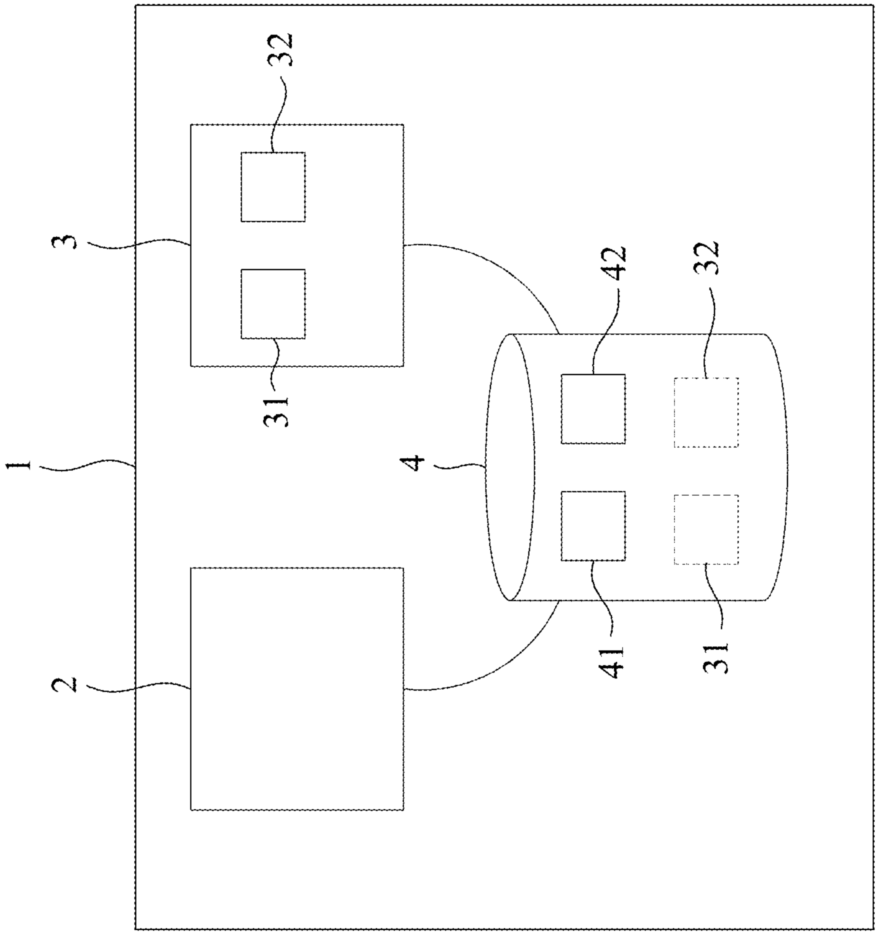
FIG. 4 is a schematic view illustrating an embodiment of the artificial intelligence-enabled algorithm system of the present invention and operation thereof.

FIG. 4 is a schematic view illustrating an embodiment of the artificial intelligence-enabled ECG algorithm system of the present invention and operation thereof. As shown in FIG. 4, the artificial intelligence-enabled ECG algorithm system 1 includes an information processing module 2, a CNN module 3, and a database 4.

The information processing module 2: the information processing module 2 cooperates with the CNN module 3 and the database 4, classifies dataset 41 stored and temporarily stored in the database 4, divides the dataset 41 into a training set, a validation set, and a test set, and processes the dataset of the training set, validation set, and test set, so that these processed data are sent to the CNN module 3 to allow the CNN module 3 to use the artificial intelligence-enabled electrocardiogram algorithm system and method 31 of the present invention to generate an evaluation model 32 for identifying VPC patients during NSR period for the CNN module.

The CNN module 3: the information processing module 2 transmits the processed data to the CNN module 3, so that the CNN module 3 can use the artificial intelligence-enabled electrocardiogram algorithm system and method 31 of the present invention to generate an evaluation model 32 for identifying VPC patients during NSR period for the CNN module 3; the CNN module 3 uses the evaluation model 32 for identifying VPC patients during NSR, in combination with the information processing module 2 and the patient dataset 42 stored in the database 4, to detect some minimal change in the electrocardiogram of sinus rhythm when the patient is without VPC episodes so that early treatment can provided to reduce the risk of heart failure or sudden death in patients.

The database 4: the database 4 can store and/or temporarily the store datasets 41, and the datasets 41 are divided into training sets, validation sets, and test sets, depending on actual applications, and also store/temporarily store the datasets 41 of the patients, the artificial intelligent-enabled ECG algorithm 31 of the present invention, and the evaluation model 32 for identifying VPC patients during NSR.

Depending on the implementation, the information processing module 2 and/or the CNN module 3 comprise at least one of electronic hardware, firmware, and software, and cooperates with the processor (not shown) of the system/device where the artificial intelligence-enabled electrocardiogram algorithm system 1 is located; and the database 4 is located in a storage module (not shown) of the system/device where the artificial intelligence-enabled electrocardiogram algorithm system 1 is located.

Herein, the information processing module 2 cooperates with the database 4 and/or the CNN module 3 to collect data. For example, the data are collected from January 2021 to October 2021 on the patients diagnosed with VPC from the National Taiwan University Hospital. Initially, 398 patients were diagnosed with VPC, and from which 2515 ECG records were collected and examined. 1617 ECG records in normal sinus rhythm without VPC are analyzed (i.e., the ECG records from patients not diagnosed with VPC), and these 1617 ECG records were double-checked by two cardiologists, and labeled as sinus rhythm from patients with VPC. For the control group, 2090 ECG records from 1053 patients were collected and screened; and finally, 753 normal ECG records from 387 patients were extracted and labeled as normal sinus rhythm (NSR). After finishing the data collection and analysis step, all the data will be stored/temporarily stored in the database 4.

The information processing module 2 cooperates with the database 4 and/or the CNN module 3 to classify and divide the dataset 41 stored/temporarily stored in the database 4 into a training set, a validation set, and a test set. First, 50 ECG records are randomly selected as the validation set, another 100 ECG records are selected as the test set, and the remaining ECG records are assigned to the training set. It is important that data from the same patient cannot be in more than one dataset, otherwise the credibility of the final results will be affected.

The information processing module 2 cooperates with the database 4 and/or the CNN module 3, and adopts the standard 12-lead ECG format for the collected ECG records, including leads I, II, III, V1-6. aVR, aVL, aVF and long lead II (MAC2000 resting ECG system, GE Healthcare), all recorded at a frequency of 500 Hz and for a duration of 2.5 seconds.

Figure 5:
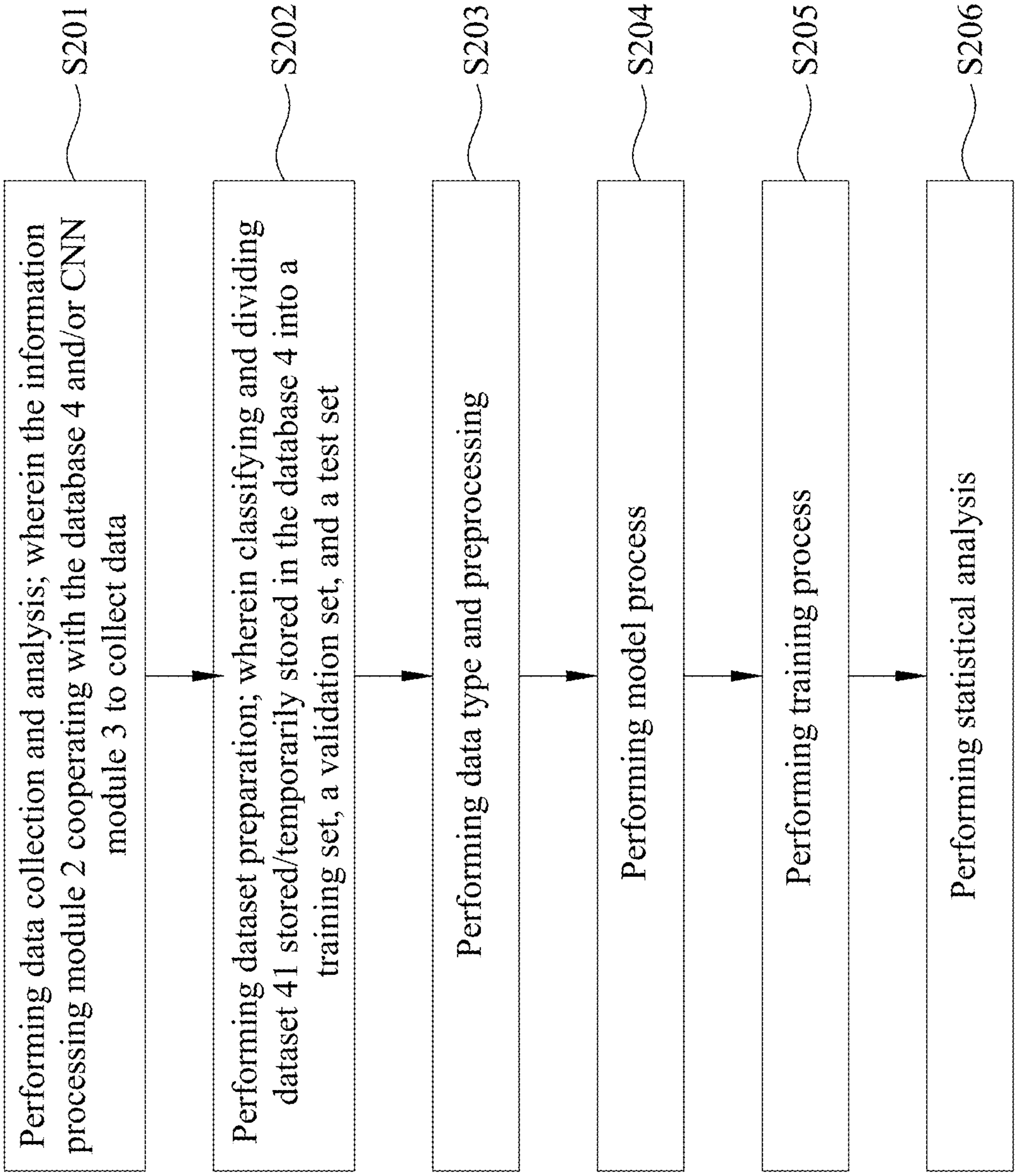
FIG. 5 is a flow chart for illustrating a process step of using an embodiment of the artificial intelligence-enabled electrocardiogram algorithm system of the present invention as in FIG. 4 to execute an artificial intelligence-enabled electrocardiogram algorithm method.

Herein, during the electrocardiogram image processing procedure before the electrocardiogram image data output, the red grid background of the electrocardiogram image is removed and processed, so that the entire image is accurately focused on the electrocardiogram signal (as shown in FIG. 5); including, inputting the standard 12-lead electrocardiogram image; removing the red background of the 12-lead ECG image; cropping the image to focus on the ECG signal.

Afterwards, the information processing module adjusts the electrocardiogram image to 512×256×3 pixels, and the two-dimensional electrocardiogram image is converted into one-dimensional time series data; an input data size of 1250×12 pixels is inputted to the CNN of the CNN module 3 to perform image recognition.

Converting 2D ECG image to 1D time-series digital data with the ECG data input format is as follows:

a. Remove the red grid background of the 12-lead ECG, and convert the ECG image to a grayscale image;
b. Inverse the pixel intensity of the gray scale image, and scale the pixel intensity to a gray level between 0 to 255. Cut the image vertically into four sub-images according to the "start" and "end" positions of each lead. The four sub-images contain 4 ECG tracings;
c. Scan the sub-image pixel-by-pixel and record the positions of the pixels where the pixel intensity is equal to 255, which are the brightest pixels representing ECG tracings. For each detected brightest pixel, the X-coordinate is assigned as the corresponding time point and the Y-coordinate as the waveform amplitude of an ECG data point;
d. The pixel coordinates of the ECG data points are then sequentially grouped to reconstruct a continuous ECG signal, and the 2D ECG image is thus digitized into 1D time-series data;
e. After pixel-by-pixel scanning again, the X-coordinate of the 1D time-series data is formatted to 250 pixels (250 time points for each ECG lead tracing). The interpolation operation is used to perform up-sampling on the time series data to obtain 1250 time points, corresponding to sampling at a standard 12-lead ECG sampling rate (500 Hz, 2.5 seconds);
f. IIR low-pass filter is used for filtering noise (cutoff frequency=15 Hz, order=3); and
g. Normalize the magnitude of each ECG lead tracing to a uniform scale.

The information processing module 2 cooperates with the database 4 and/or the CNN module 3, and the CNN module 3 utilizes algorithm 31 of the present invention to establish an evaluation model 32 for identifying VPC patients during NSR required by the CNN module 3, which will be established based on the dimensional features of the data format.

Herein, for two-dimensional image data, five network computer architectures are used, including VGG16, ResNet0V2, Inception V3, InceptionResNetV2, and Xception, to utilize the ImageNet part of the CNN for optimal image recognition.

The structure of CNN:

a. Two-dimensional image data is processed through five network computer architectures including VGG16, ResNet50V2, Inception V3, InceptionResNetV2, and Xception to obtain the optimal image recognition in the ImageNet part of CNN, and then flatten into GlobalAveragePooling (GAP); CNN, after extracting the features of the image data, flattens the signal by busing GlobalAveragePooling (GAP), and connects to another dense layer; Dropout is added to avoid overfitting later (dropout rate=0.5); and finally, another dense layer of size 2 is added, which presents two types of results as an output layer (VPC and NSR);
b. A dense layer is connected with a single input from 2D image data; dropout is added to avoid overfitting (dropout rate=0.5), and another dense layer of size 2 is added to obtain an output layer (VPC: Ventricular premature contractions; NOR: normal rhythm); for time series data, performing model processing by using single-input and multi-input computer architectures; initially, the convolution kernel (kernel) is changed to a one-dimensional kernel, and CNN tries different kernel sizes; stride is set to 3, and the moving window of the convolution kernel spans three grids at a time; each convolution block comprises a one-dimensional CNN activated by BatchNormalization and ReLU; the setting of Maxpooling is that the pooling size is equal to 5, and the stride is equal to 3; the feature signal is extracted by the CNN layer, and then flattened by GAP; the output features of the single-input model are directly connected to dropout (dropout rate=0.5) to avoid overfitting; on the other hand, the multi-input model will merge the features of the 12 channels together and connect to a dense layer (dense size=2) to obtain the output result;
c. The signal of time series data is extracted by CNN layer and then flattened by GAP. The output features of the single-input model are directly connected to dropout (dropout rate=0.5), and the multi-input model of the features of 12 channels is merged to obtain the output result (dense size=2), (GAP is the global average pool).

During a training procedure, Google Colaboratory (Colab) with a high random access memory graphics processing unit environment is used as a training platform; the Colab is supported by Python 3.8 and Tensorflow for CNN training process. The keras application programming interface (API), which is a deep learning API written in Python, is also used to build CNN models and ImageNet races for migration and learning.

During statistical analysis, the optimal cut points and measures for diagnosing the performance include accuracy, sensitivity, specificity, positive predictive value, negative predictive value, and area under the curve (AUC) of receiver operating feature (ROC) curve. All reports have two-sided 95% confidence intervals. Data were statistically analyzed by IBM SPSS (version 25 for Windows, Armonk, New York).

FIG. 5 is a flow chart illustrating an embodiment of the artificial intelligence-enabled ECG algorithm system as shown in FIG. 4 to execute a process step of the artificial intelligence-enabled ECG algorithm method. As shown in FIG. 5, first, step 201 is to perform data collection and analysis, wherein when the information processing module 2 performs the data collection and analysis, the information processing module 2 cooperates with the database 4 and/or the CNN module 3 to collect data; and then proceed to step 202.

Herein, in step 201, when the information processing module 2 performs data collection and analysis, the information processing module 2 cooperates with the database 4 and/or the CNN module 3 to collect data. For example, the data are collected from January 2021 to October 2021 on the patients diagnosed with VPC from the National Taiwan University Hospital. Initially, 398 patients were diagnosed with VPC, and from which 2515 ECG records were collected and examined. 1617 ECG records in normal sinus rhythm without VPC are analyzed (i.e., the ECG records from patients not diagnosed with VPC), and these 1617 ECG records were double-checked by two cardiologists, and labeled as sinus rhythm from patients with VPC. For the control group, 2090 ECG records from 1053 patients were collected and screened; and finally, 753 normal ECG records from 387 patients were extracted and labeled as normal sinus rhythm (NSR). After finishing the data collection and analysis step, all the data will be stored/temporarily stored in the database 4.

Step 202 is to prepare the data, wherein the information processing module 2 cooperates with the database 4 and/or the CNN module 3 to classify and divide the dataset 41 stored/temporarily stored in the database 4 into a training set, a validation set, and a test set; and then proceed to step 203.

Herein, in step 202, 50 ECG records are randomly selected as a validation set, and 100 ECG records are selected as a test set, and the remaining data are assigned to the training set. It is important that data from the same patient cannot be in more than one dataset, otherwise the credibility of the final results will be affected.

Step 203 is to perform data type and preprocessing, wherein the information processing module 2 cooperates with the database 4 and/or the CNN module 3, and adopts the standard 12-lead ECG format for the collected ECG records, including leads I, II, III, V1-6, aVR, aVL, aVF and long lead II (MAC2000 resting ECG system, GE Healthcare), and all recordings are measured at a frequency of 500 Hz with a duration of 2.5 seconds; and then proceed to step 204.

Herein, in step 203, during the electrocardiogram image processing procedure before the electrocardiogram image data output, the red grid background of the electrocardiogram image is removed and processed, so that the entire image is accurately focused on the electrocardiogram signal (as shown in FIG. 6); including, inputting the standard 12-lead electrocardiogram image; removing the red background of the 12-lead ECG image; cropping the image to focus on the ECG signal.

Figure 7:
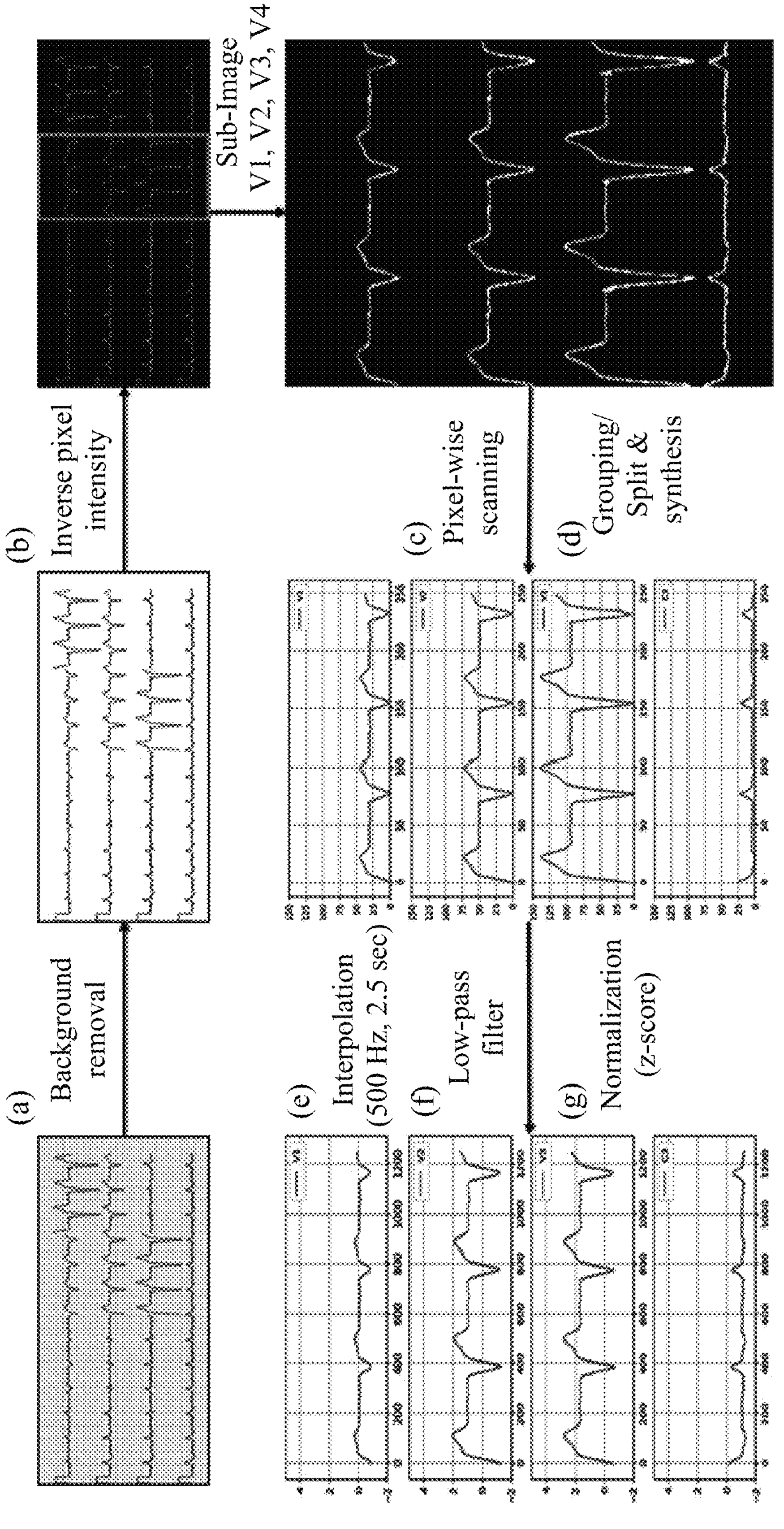
FIGS. 7(*a*)-(*g*) are schematic views illustrating the ECG data input format described in FIGS. 3 and 4.

Afterwards, the information processing module adjusts the electrocardiogram image to 512×256×3 pixels, and the two-dimensional electrocardiogram image is converted into one-dimensional time series data; an input data size of 1250×12 pixels is inputted to the CNN of the CNN module 3 to perform image recognition (as shown in FIG. 7).

Converting 2D ECG image to 1D time-series digital data with the ECG data input format is as follows:

a. Remove the red grid background of the 12-lead ECG, and convert the ECG image to a grayscale image;
b. Inverse the pixel intensity of the gray scale image, and scale the pixel intensity to a gray level between 0 to 255. Cut the image vertically into four sub-images according to the “start” and “end” positions of each lead. The four sub-images contain 4 ECG tracings;

c. Scan the sub-image pixel-by-pixel and record the positions of the pixels where the pixel intensity is equal to 255, which are the brightest pixels representing ECG tracings. For each detected brightest pixel, the X-coordinate is assigned as the corresponding time point and the Y-coordinate as the waveform amplitude of an ECG data point;

d. The pixel coordinates of the ECG data points are then sequentially grouped to reconstruct a continuous ECG signal, and the 2D ECG image is thus digitized into 1D time-series data;

e. After pixel-by-pixel scanning again, the X-coordinate of the 1D time-series data is formatted to 250 pixels (250 time points for each ECG lead tracing). The interpolation operation is used to perform up-sampling on the time series data to obtain 1250 time points, corresponding to sampling at a standard 12-lead ECG sampling rate (500 Hz, 2.5 seconds);

f. IIR low-pass filter is used for filtering noise (cutoff frequency=15 Hz, order=3); and g. Normalize the magnitude of each ECG lead tracing to a uniform scale.

Step 204 is to perform the model process, wherein the information processing module 2 cooperates with the database 4 and/or the CNN module 3, and the CNN module 3 utilizes the algorithm method 31 of the present invention to establish an evaluation model 32 for identifying VPC patients during NSR required by the CNN module 3, which will be established based on the dimensional features of the data format. Herein, for two-dimensional image data, five network computer architectures are used, including VGG16, ResNet0V2, InceptionV3, InceptionResNetV2, and Xception, to utilize the ImageNet part of the CNN for optimal image recognition; and then proceed to step 205.

Herein, the structure of CNN:

a. Two-dimensional image data is processed through five network computer architectures including VGG16, ResNet50V2, Inception V3, InceptionResNetV2, and Xception to obtain the optimal image recognition in the ImageNet part of CNN, and then flatten into GlobalAveragePooling (GAP); CNN, after extracting the features of the image data, flattens the signal by busing GlobalAveragePooling (GAP), and connects to another dense layer; Dropout is added to avoid overfitting later (dropout rate=0.5) (as shown in FIG. 8*b*); and finally, another dense layer of size 2 is added, which presents two types of results as an output layer (VPC and NSR) (as shown in FIG. 8*b*);

b. A dense layer is connected with a single input from 2D image data; dropout is added to avoid overfitting (dropout rate=0.5), and another dense layer of size 2 is added to obtain an output layer (VPC: Ventricular premature contractions; NOR: normal rhythm); for time series data, performing model processing by using single-input and multi-input computer architectures; initially, the convolution kernel (kernel) is changed to a one-dimensional kernel, and CNN tries different kernel sizes; stride is set to 3, and the moving window of the convolution kernel spans three grids at a time; each convolution block comprises a one-dimensional CNN activated by BatchNormalization and ReLU; the setting of Maxpooling is that the pooling size is equal to 5, and the stride is equal to 3; the feature signal is extracted by the CNN layer, and then flattened by GAP; the output features of the single-input model are directly connected to dropout (dropout rate=0.5) to avoid overfitting (as shown in FIG. 8*c*); on the other hand, the multi-input model will merge the features of the 12 channels together and connect to a dense layer (dense size=2) to obtain the output result (as shown in FIG. 8*c*);

c. The signal of time series data is extracted by CNN layer and then flattened by GAP. The output features of the single-input model are directly connected to dropout (dropout rate=0.5), and the multi-input model of the features of 12 channels is merged to obtain the output result (dense size=2), (GAP is the global average pool).

Step 205 is to perform a training procedure, wherein Google Colaboratory (Colab) with a high random access memory graphics processing unit environment is used as a training platform; the Colab is supported by Python 3.8 and Tensorflow for CNN training process. The keras application programming interface (API), which is a deep learning API written in Python, is also used to build CNN models and ImageNet races for migration and learning; and then proceed to step 206. The settings and training parameters of the API are shown in Table 1.

TABLE 1

Application programming interfaces and parameter setting

| API or Parameters | Name | Setting |
|---|---|---|
| Callback | EarlyStopping | Patience = 250 |
| Optimizer | Adam | Learning rate = 0.0011 |
| Metrics | Accuracy | — |
| Losses | Categorical Crossentropy | — |
| Epochs | — | 400 |
| Batch size | — | 32 |

API: Application Programming Interface

Step 206 is to perform statistical analysis, wherein the optimal cut points and measures for diagnosing the performance include accuracy, sensitivity, specificity, positive predictive value, negative predictive value, and area under the curve (AUC) of receiver operating feature (ROC) curve. All reports have two-sided 95% confidence intervals. Data were statistically analyzed by IBM SPSS (version 25 for Windows, Armonk, New York).

Figures 6A, 6B, 6C:
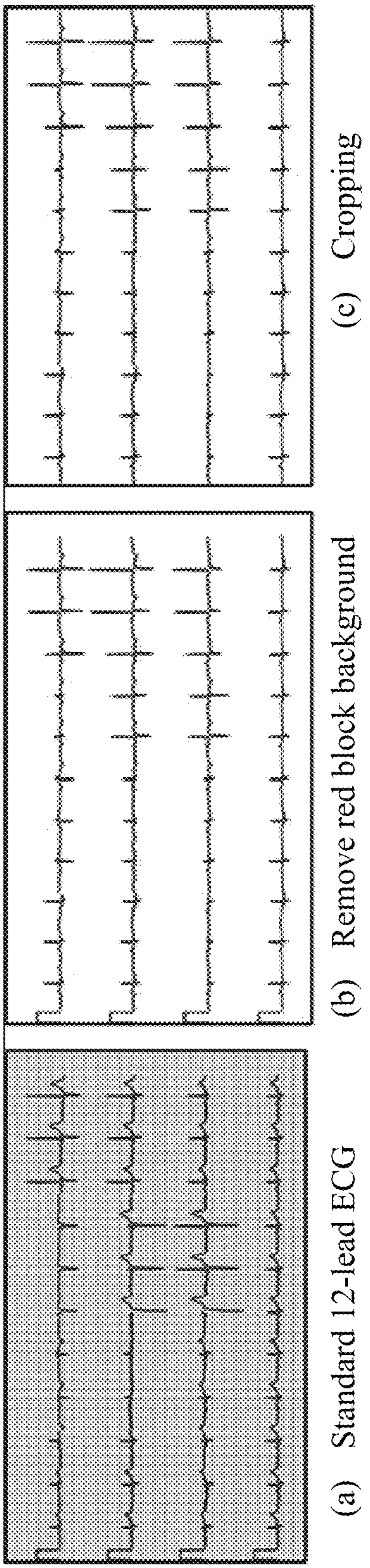
FIGS. 6A-6C are schematic views illustrating the process of ECG image processing prior to input described in FIGS. 4 and 5.

FIGS. 6A-6C are schematic views illustrating the preprocessing ECG image prior to inputting described in FIGS. 4 and 5. As shown in the figures, FIG. 6A is a standard 12-lead ECG image. FIG. 6B shows removing the red background of the 12-lead ECG image. FIG. 6C shows cropping the image to focus on the ECG signal.

FIGS. 7(*a*)-(*g*) are schematic views illustrating the ECG data input format described in FIGS. 4 and 5. The information processing module adjusts the electrocardiogram image to 512×256×3 pixels, and the two-dimensional electrocardiogram image is converted into one-dimensional time series data; an input data size of 1250×12 pixels is inputted to the CNN of the CNN module 3 to perform image recognition.

FIG. 7(*a*): Remove the red grid background of the 12-lead ECG, and convert the ECG to a grayscale image.

FIG. 7(*b*): Reverse the pixel intensity, and the pixel intensity is 255 pixels. Cut the image vertically into four sub-images according to the “start” and “end” positions of each lead.

FIG. 7(*c*): Scan the sub-image pixel-by-pixel and record the position of the pixels where the pixel intensity is equal to 255.

FIG. 7(*d*): Group the nearest position of the data signal, each column is divided into four values, and all values of the column are synthesized into four lists in each lead, and the signal is converted into a time series format.

FIG. 7(*e*): The column of each sub-image comprises 250 pixels. After pixel-by-pixel scanning, a lead with 250 time series data is formatted. The interpolation operation is used to perform up-sampling on the time series data (500 Hz, 2.5 seconds).

FIG. 7(*f*): IIR low-pass filter is used for filtering noise (cutoff frequency=15 Hz, order=3).

FIG. 7(*g*): Normalize the size of each lead to a uniform scale.

Figure 8A:
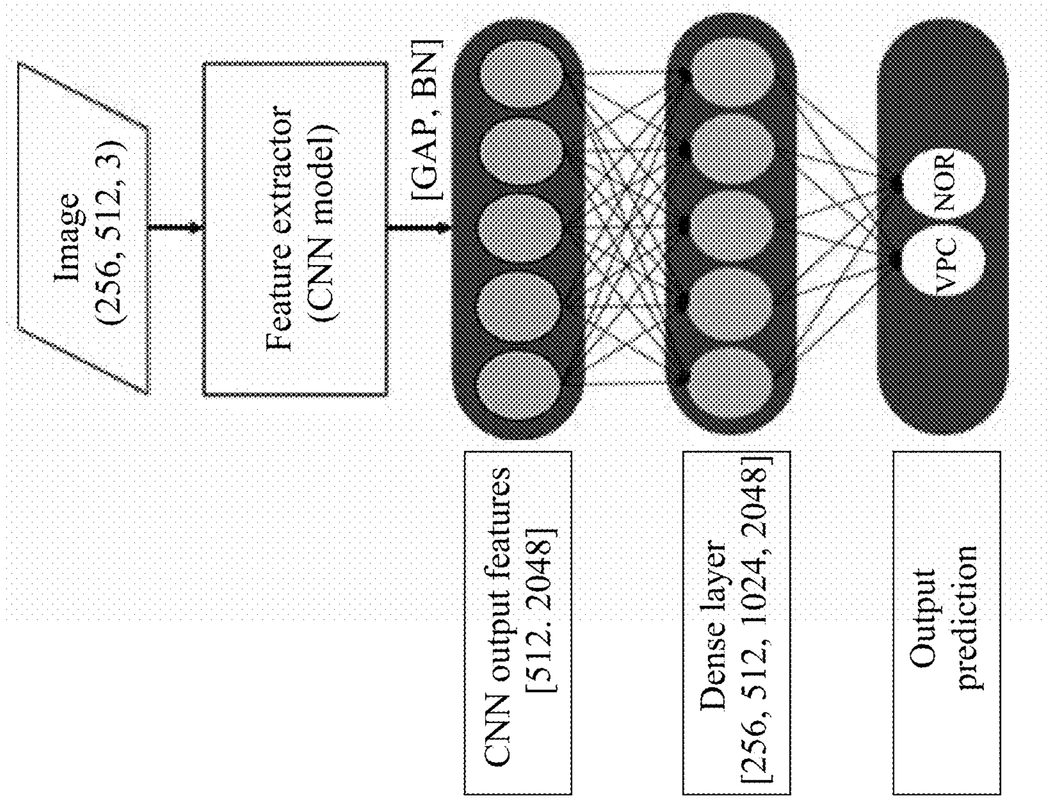
FIG. 8A is a schematic view illustrating the architecture of the convolutional neural network (CNN) illustrated in FIGS. 4 and 5.
Figure 8B:
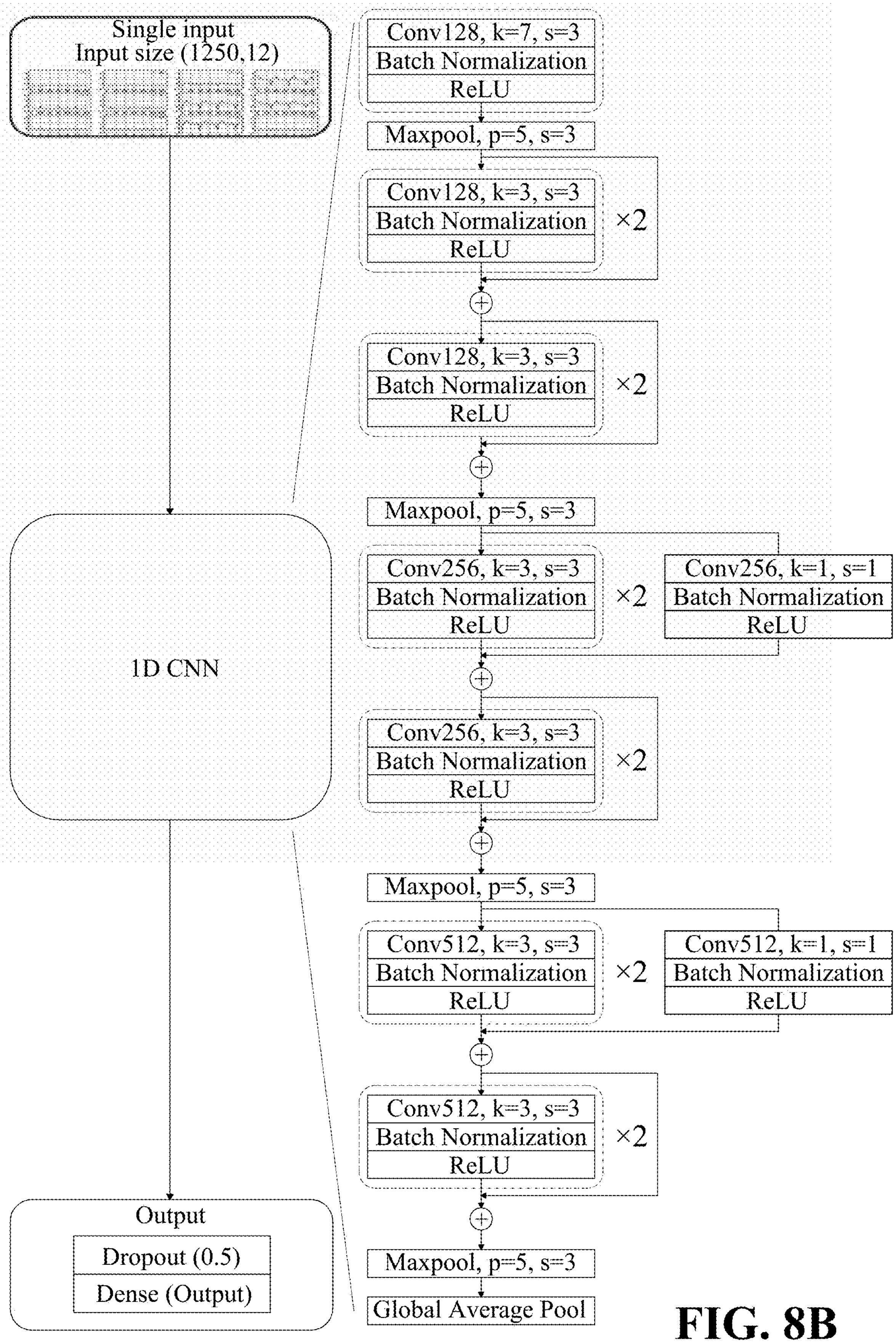
FIG. 8B is a schematic view illustrating the dense layers illustrated in FIGS. 4 and 5 connecting a single input from 2D image data.
Figure 8C:
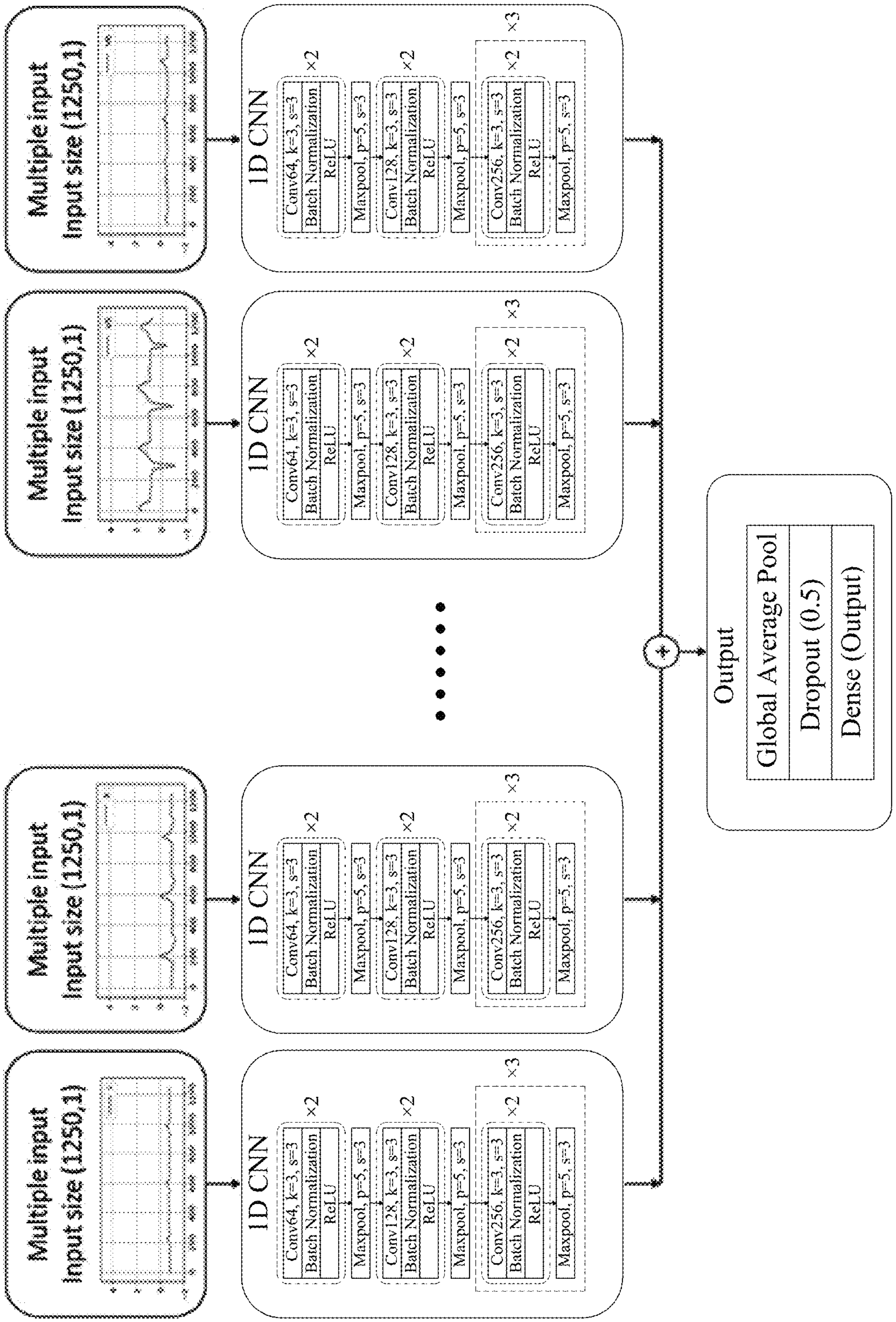
FIG. 8C is a schematic view illustrating that the signals of the time series data illustrated in FIGS. 4 and 5 extracted by CNN layers and flattened by GAP.

FIG. 8A is a schematic view showing the architecture of the convolutional neural network (CNN) described in FIG. 4 and FIG. 5. As shown in the figure, the CNN model is established according to the dimensional features of the data format. For 2D image data, five network computer architectures, including VGG16, ResNet0V2, Inception V3, InceptionResNetV2, and Xception are used to achieve the optimal image recognition using the ImageNet part of CNN (FIG. 8A).

The two-dimensional image data is processed through the five network computer architectures, VGG16, ResNet50V2, InceptionV3, InceptionResNetV2, and Xception, to obtain the optimal image recognition in the Image Net part of CNN, and then flattened into GlobalAveragePooling (GAP).

FIG. 8B is a schematic view showing the dense layers illustrated in FIGS. 4 and 5 connecting a single input from two-dimensional image data. As shown in the figure, after CNN extracts the features of the image data, the signal is flattened by GlobalAveragePooling (GAP), and another dense layer is connected. Dropout is added to avoid overfitting later (dropout rate=0.5).

Finally, another dense layer of size 2 is added, which represents two types of results as output layers (VPC and NSR).

Dense layers is connected to a single input from two-dimensional image data. Dropout is added to avoid overfitting (dropout rate=0.5) and another dense layer of size 2 was added to obtain the output layer. (VPC: ventricular premature beats; NOR: normal rhythm).

For time series data, single-input and multi-input computer architectures were used for model processing. Initially, CNN experiments with different kernel sizes by changing the convolution kernels to 1D kernels. With stride set to 3, the moving window of the convolution kernel spans three grids at a time. Each convolutional block consists of a 1D CNN powered by BatchNormalization and ReLU.

FIG. 8C is a schematic view showing the signal of the time series data illustrated in FIGS. 4 and 5 extracted by CNN layer and flattened by GAP. As shown in the figure, the setting of Maxpooling is that the pooling size is equal to 5, and the stride is equal to 3; the feature of the signal is extracted by the CNN layer, and then flattened by GAP. The output features of the single-input model are directly connected to dropout (dropout rate=0.5) to avoid overfitting; on the other hand, the multi-input model will merge the features of the 12 channels together and connect to a dense layer (dense size=2) to obtain the output result.

The signal of time series data is extracted by CNN layer and flattened by the GAP. The output features of the single-input model are directly connected to dropout (dropout rate=0.5), and the multi-input model of the features of 12 channels is merged to obtain the output result (dense size=2).

Regarding FIG. 1 to FIGS. 8A-8C, and relevant disclosed content:

The performance of the image input model:

Among all included patients, the mean age at first ECG is 62.4 years old (SD 14.3), and 750 (52%) patients are male. Different pretrained CNN models with different sizes of dense and fully connected layers are evaluated using different test sets. Five network computer architectures, including VGG16, ResNet50V2, InceptionV3, InceptionResNetV2, and Xception, are used to select the optimal model with the highest accuracy for the subsequent training process.

Finally, InceptionV3, a CNN model connected with dense layers (size=512), is chosen as the kernel CNN model for the image format dataset. Compared to other combinations, the accuracy is the highest (Accuracy=0.895, Sensitivity=0.907, Specificity=0.883, 95% CI) (as shown in FIG. 9).

Figure 9:
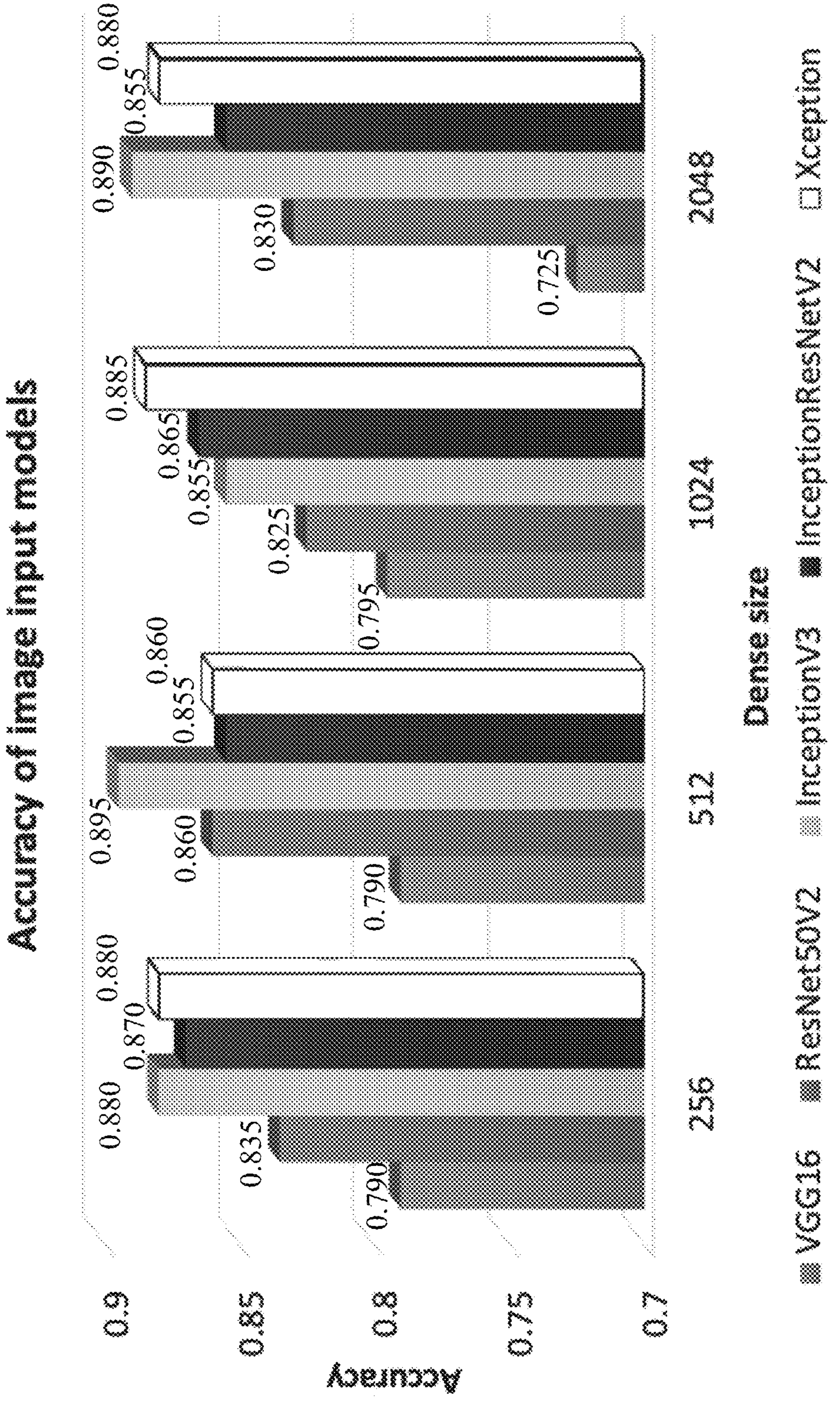
FIG. 9 is a schematic view illustrating the accuracy of the image input model.

FIG. 9 is a schematic view illustrating the accuracy of the image input model. The figure shows the accuracy of the CNN model with different image inputs with different connection layer sizes.

Figure 10:
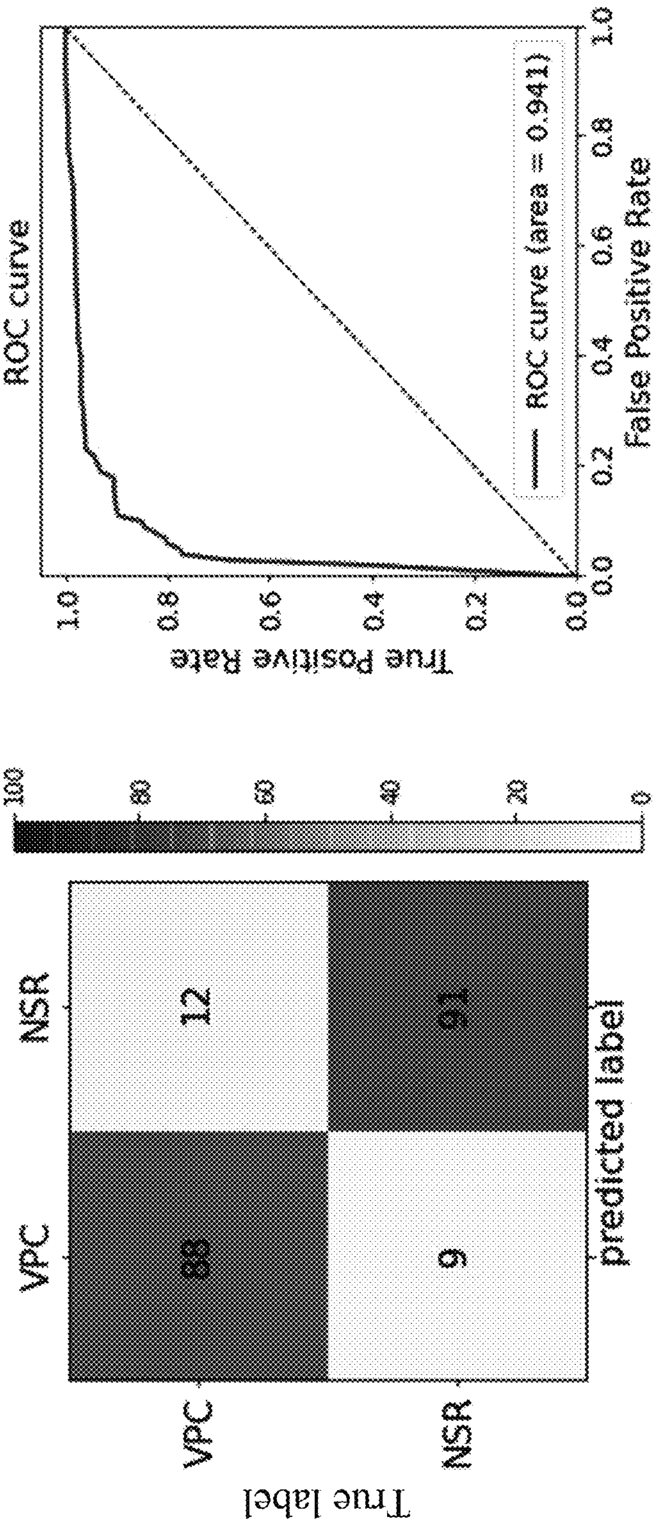
FIG. 10 is a schematic view illustrating the AUC of the ROC is 0.941 for the model architecture.

FIG. 10 is a schematic view showing the AUC of the ROC of the model architecture is 0.941. The figure shows the AUC dense layer (size=512) of the combination of the InceptionV3 CNN model and the model's ROC, (CNN: Convolutional Neural Network, AUC: Area Under the Receiver Operating Feature Curve, ROC: Receiver Operating feature curve).

In terms of the performance of the time series input model:

For time series data, convolution kernels of different sizes were evaluated to find the optimal combination. The optimal kernel size for executing the single-input model is 7, while the optimal kernel size for the multi-input model is 11, as shown in Table 2.

TABLE 2

Time-series data for the single and multi-input models

| Kernel size | Accuracy | ROC AUC | Sensitivity | Specificity |
|---|---|---|---|---|
| Single-input (1250 × 12) | | | | |
| 3 | 0.795 | 0.866 | 0.798 | 0.792 |
| 5 | 0.815 | 0.886 | 0.889 | 0.765 |
| 7 | 0.840 | 0.889 | 0.886 | 0.804 |
| 9 | 0.835 | 0.893 | 0.885 | 0.796 |
| 11 | 0.835 | 0.895 | 0.868 | 0.807 |
| Multi-input (1250 × 1) × 12 | | | | |
| 3 | 0.865 | 0.920 | 0.884 | 0.848 |
| 5 | 0.875 | 0.928 | 0.895 | 0.857 |
| 7 | 0.860 | 0.929 | 0.875 | 0.846 |
| 9 | 0.850 | 0.920 | 0.917 | 0.802 |
| 11 | 0.880 | 0.929 | 0.896 | 0.865 |

ROC AUC: area under the receiver operating characteristic curve;
VPC: ventricular premature complex In the multi-input model, the CNN channel needs to analyze the signals of all 12 leads simultaneously. The complexity is relatively higher than the single-input model that only needs to analyze the signal of one lead. In addition, multi-input models use parallelization of analysis. Therefore, the accuracy of the multi-input model is 4% higher than that of the single-input model (single-input model: 0.840, multi-input model: 0.880, 95% CI), as shown in Table 3.

TABLE 3

| Compare both single-input and multi-input models | | | | | |
|---|---|---|---|---|---|
| Data type | Model | Acc. | ROC AUC | Sensitivity | Specificity |
| Time series | ResNet50V2 (Single-input) | 0.840 | 0.889 | 0.886 | 0.804 |
| Time series | ResNet50V2 (Multi-input) | 0.880 | 0.929 | 0.896 | 0.865 |

Acc: accuracy;
ROC AUC: area under the receiver operating characteristic curve;
VPC: ventricular premature complex The accuracy of the multi-input time series model is still lower than but very close to that of the image input model (0.880 vs 0.895).

When the artificial intelligence-enabled ECG algorithm system and method thereof of the present invention are actually implemented:

AI-enabled ECGs recorded during normal sinus rhythm are found to perform well in identifying the presence of VPC (AUC 0.941). Accuracy is comparable to prior arts using an AI-enabled ECG to identify AF during normal sinus rhythm (AUC 0.87-0.90), and is also comparable to other medical screening tests, such as B-type natriuretic peptide, for heart failure (AUC 0.60-0.70), cervical cancer Pap smear (AUC 0.70), and CHA2DS2-VASc skernel stroke risk (AUC 0.57-0.72).

Regarding the importance of VPC detection during sinus rhythm:

Although VPC appears to be benign, it is associated with an increase in cardiovascular events. From the Framingham Heart Tracker Study, the Multiple Risk Factor Intervention Trial (MRFIT), and the Atherosclerosis Risk in Communities (ARIC) study, VPC has been shown to be an independent risk factor for death in patients without structural heart disease.

VPC is also known to induce ventricular tachycardia/fibrillation and lead to sudden cardiac death (SCD) or unexplained syncope in patients without ischemic cardiomyopathy. In addition, patients with frequent VPCs (defined as >1 VPC on a 10-second ECG or >30 VPCs in an hour) are associated with predisposing to heart failure and sudden cardiac death. Patients with frequent VPCs are at risk for VPC-induced cardiomyopathy even if they are asymptomatic.

The ability to identify undetected VPC with inexpensive, widely available point-of-care tests (ECG recorded during normal sinus rhythm) has important practical implications, especially for VPC screening, or for the diagnosis and treatment of unwell patients with unexplained syncope or chest discomfort, especially those with a family history of SCD.

The present invention demonstrates the ability to leverage modern computing techniques, large datasets, nonlinear models, and automated feature extraction using convolutional layers to potentially improve the diagnosis and treatment of life-threatening diseases. When VPC is found, treatment can be started early.

Catheter ablation significantly improved the outcomes. A plurality of large, prospective, randomized studies have also shown that implantable cardioverter-defibrillator (ICD) implantation improves survival in patients with life-threatening ventricular arrhythmias.

Long-term ambulatory monitoring of patients with unexplained syncope or SCD can identify VPC. Therefore, short-term ECG monitoring may fail to detect VPC, and until VPC is detected, a significant proportion of patients cannot prevent SCD. However, long-term ECG monitoring is expensive and can be burdensome to the patient and the clinician.

Thus, the present invention allows patients to benefit from simple monitoring and is of value to patients. The present data suggest that a simple, inexpensive, and non-invasive 10-second test, such as, an artificial intelligence-enhanced standard ECG, may overcome the difficulty of identifying VPC detection.

In terms of the dimensions of the 12-lead ECG data:

When applying CNN analysis in 12-lead ECGs, the one-dimensional approach treats the ECG data as a time-series format. CNNs, on the other hand, use kernels during 2D data processing to extract all the features of a 12-lead ECG. CNN kernels can be activated by specific functions and then identified by neural network analysis.

The two-dimensional analysis thus treats the data as an image, more akin to the way a cardiologist interprets a 12-lead ECG. However, the 2D data volume is huge and much more complex than the 1D data format.

Therefore, the common AI tools cannot analyze 12-lead ECGs stored in the image format. To over the difficulties in analyzing these large and complex two-dimensional data, various combinations of available networks and different computer architectures are used to obtain the optimal accuracy for VPC predictions of CNN models.

One of the important features of the present invention is CNN-enabled two-dimensional data prediction VPC model, which has never been successfully performed by prior art. After optimizing the input model architecture, the two-dimensional CNN model of the present invention can identify abnormal ECG and classify high-risk groups during VPC without seizures.

From prior arts, AI-driven algorithms have been applied to automatic diagnosis of various diseases, such as myocardial infarction requiring urgent blood line reconstitution, systolic heart failure, subtle changes in potassium and atrial fibrillation in high-risk groups.

However, most of these studies are based on single-lead ECG or one-dimensional (time series) datasets. From the results of the present invention, CNN models derived from 12-lead ECG and 2D data formats are able to reliably and automatically predict VPC onset with even better accuracy than 1D or time series results (0.895 vs. 0.880). The present study demonstrates the possibility of implementing a CNN model to identify VPC patients using 1D or 2D data.

Regarding the mechanism of AI-enabled identification of VPC patients during normal sinus rhythm:

Emphasize that structural changes in the heart that cause VPC, which may include cardiomyocyte hypertrophy, fibrosis, and ventricular enlargement, and may result in subtle ECG changes that can be used to predict underlying VPC. This is very similar to using a signal-averaged ECG to detect late ventricular potentials that the human eye cannot see with a single ECG.

Furthermore, although there are few reports on ECG, mild intraventricular conduction block may be associated with mild myocardial fibrosis and risk of VPC or SCD. Therefore, the wavelets on the ECG may be smaller than those observable by the human eye, but our findings reflect the presence of subtle regional conduction blocks in these patients.

A neural network trained on a large number of ECGs with sufficient depth to extract subtle features that are invisible to humans may be powerful enough to recognize these subtle features. Finally, AI-enabled ECGs have been reported to predict left ventricular function, and lower left ventricular ejection fraction has been shown to be a strong predictor of ventricular arrhythmias.

With the AI-enabled ECG algorithm system and method thereof of the present invention:

CNN neural networks are shown to be a promising tool for comprehensive human-like interpretation of ECGs. Deep learning CNN models show satisfactory performance in high-dimensional datasets for VPC prediction. It will have enormous potential deployment in the clinical arena and a largely unpredictable impact in the future.

However, a key limitation of existing neural networks is interpretability. Identifying these features is important as they may provide new discoveries of pathogenic mechanisms that may provide new therapeutic targets. Finding ways to peer into this so-called black box of neural network interpretation is an ongoing area of active investigation.

Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. An artificial intelligence-enabled (AI-enabled) electrocardiogram (ECG) algorithm method, applicable to identifying patients with ventricular premature contraction (VPC) under an environment during sinus rhythm, comprising the following steps:

using an ECG machine having 12 leads to collect a plurality of ECG datasets from the patients, each of the ECG datasets including one-dimensional ECG raw data and an ECG image;

classifying and dividing the ECG datasets into a training set, a validation set, and a test set;

performing image processing to remove and process background of the ECG image, and converting the ECG image into one-dimensional time-series data; and performing at least one of AI and convolutional neural network (CNN) processing based on the one-dimensional time-series data by using an AI-enabled ECG algorithm to establish an evaluation model for identifying VPC patients during normal sinus rhythm (NSR);

wherein the ECG image is a 12-lead ECG image and the step of performing image processing and converting the ECG image into the one-dimensional time-series data further comprises the following processing steps:

a. removing a red grid background of the 12 leads in the ECG image and converting the ECG image to a gray-scale image;

b. inversing intensities of pixels of the gray-scale image and scaling the intensities of the intensity inversed pixels to form an intensity inversed image with a gray scale of 0 to 255 gray levels, and spatially partitioning the intensity inversed image into four sub-images according to start and end positions of each of the 12 leads based on a predefined 12-lead layout, the four sub-images containing 4 ECG tracings;

c. scanning each of the four sub-images along a horizontal time axis pixel by pixel to identify a representative pixel having a maximum intensity equal to 255 gray levels for each vertical column of pixels, and recording positions of the representative pixels of each sub-image to represent the 4 ECG tracings; mapping X and Y coordinates of the identified representative pixels to construct a continuous waveform profile for each lead by assigning an X-coordinate and a Y-coordinate of each representative pixel as a time stamp and a magnitude of an ECG data point;

d. sequentially grouping ECG data points formed by the maximum intensity pixels to construct a continuous ECG signal for each ECG tracing having 250 ECG data points;

e. using an interpolation operation to perform upsampling and convert the 250 ECG data points into 1250 ECG data points, corresponding to 2.5 seconds of the one-dimensional time-series data with a standard 12-lead ECG sampling rate of 500 Hz;

f. filtering the one-dimensional time-series data using a low-pass filter, the low-pass filter having an order of 3 and a cutoff frequency at 15 Hz; and g. normalizing the magnitude of the filtered one-dimensional time-series data of each ECG tracing to a uniform scale; and wherein the evaluation model is further used by the at least one of AI and CNN processing based on the one-dimensional time-series data during NSR to detect a change in the ECG dataset of sinus rhythm when a patient is without VPC episodes so that early treatment is provided to the patient to reduce a risk of heart failure or sudden death of the patient.

2. The AI-enabled ECG algorithm method according to claim 1, wherein the ECG datasets comprise 12-lead ECG data, when applying CNN analysis to the 12-lead ECG data, the CNN uses CNN kernels to extract features of the 12-lead ECG data in a two-dimensional (2D) data processing method, and the CNN kernels are activated by a specific function and then identified by neural network analysis.

3. The AI-enabled ECG algorithm method according to claim 1, wherein in performing at least one of AI and CNN processing, the evaluation model to identify VPC patients during NSR for a CNN model is established according to preprocessed ECG two-dimensional data and dimensional features of the ECG datasets.

4. The AI-enabled ECG algorithm method according to claim 3, wherein the preprocessed ECG two-dimensional data is obtained by using five network computer architectures, including VGG16, ResNet0V2, InceptionV3, InceptionResNetV2, and Xception to use an ImageNet part of the CNN for optimal image recognition.

5. An artificial intelligence-enabled (AI-enabled) algorithm system, applicable to identifying patients with ventricular premature contraction (VPC) under an environment during sinus rhythm, comprising:

an electrocardiogram (ECG) machine having 12 leads for collecting a plurality of ECG datasets from the patients, each of the ECG datasets including one-dimensional ECG raw data and an ECG image;

a database for storing the ECG datasets, the ECG datasets being classified and divided into a training set, a validation set and a test set;

an information processing module for performing image processing to remove and process background of the ECG image, and converting the ECG image into one-dimensional time-series data; and a convolutional neural network (CNN) module cooperating with the database and the information processing module for performing at least one of AI and the CNN processing by using an AI-enabled ECG algorithm based on the one-dimensional time-series data to establish an evaluation model for identifying VPC patients during normal sinus rhythm (SNR);

wherein the ECG image is a 12-lead ECG image and the information processing module is programed to perform image processing and convert the ECG image into the one-dimensional time-series data, including the following processing steps:

a. removing a red grid background of the 12 leads in the ECG image and converting the ECG image to a gray-scale image;

b. inversing intensities of pixels of the gray-scale image and scaling the intensities of the intensity inversed pixels to form an intensity inversed image with a gray scale of 0 to 255 gray levels, and spatially partitioning the intensity inversed image into four sub-images according to start and end positions of each of the 12 leads based on a predefined 12-lead layout, the four sub-images containing 4 ECG tracings;

c. scanning each of the four sub-images along a horizontal time axis pixel by pixel to identify a representative pixel having a maximum intensity equal to 255 gray levels for each vertical column of pixels, and recording positions of the representative pixels of each sub-image to represent the 4 ECG tracings; mapping X and Y coordinates of the identified representative pixels to construct a continuous waveform profile for each lead by assigning an X-coordinate and a Y-coordinate of each representative pixel as a time stamp and a magnitude of an ECG data point;

d. sequentially grouping ECG data points formed by the maximum intensity pixels to construct a continuous ECG signal for each ECG tracing having 250 ECG data points;

e. using an interpolation operation to perform up-sampling and convert the 250 ECG data points into 1250 ECG data points, corresponding to 2.5 seconds of the one-dimensional time-series data with a standard 12-lead ECG sampling rate of 500 Hz;

f. filtering the one-dimensional time-series data using a low-pass filter, the low-pass filter having an order of 3 and a cutoff frequency at 15 Hz; and g. normalizing the magnitude of the filtered one-dimensional time-series data of each ECG tracing to a uniform scale; and wherein the evaluation model is further used by the at least one of AI and CNN processing based on the one-dimensional time-series data during NSR to detect a change in the ECG dataset of sinus rhythm when a patient is without VPC episodes so that early treatment is provided to the patient to reduce a risk of heart failure or sudden death of the patient.

6. The AI-based ECG algorithm system according to claim 5, wherein the ECG datasets comprise 12-lead ECG data, when applying CNN analysis to the 12-lead ECG data, the CNN uses CNN kernels to extract features of the 12-lead ECG data in a two-dimensional (2D) data processing method, and the CNN kernels are activated by a specific function and then identified by neural network analysis.

7. The AI-based ECG algorithm system according to claim 5, wherein in performing AI and CNN processing, the evaluation model to identify VPC patients during NSR for a CNN model is established according to preprocessed ECG two-dimensional data and dimensional features of the ECG datasets.

8. The AI-based ECG algorithm system according to claim 7, wherein the preprocessed ECG two-dimensional data is obtained by using five network computer architectures, including VGG16, ResNet0V2, InceptionV3, InceptionResNetV2, and Xception to use an ImageNet part of the CNN for optimal image recognition.

* * * * *